United States Patent
McPherson et al.

(10) Patent No.: US 8,071,336 B2
(45) Date of Patent: *Dec. 6, 2011

(54) ANTIBODY-BASED THERAPEUTICS WITH ENHANCED ADCC ACTIVITY

(75) Inventors: John M. McPherson, Hopkinton, MA (US); Tim Edmunds, Bolton, MA (US); Qun Zhou, Ashland, MA (US)

(73) Assignee: Genzyme Corporation, Cambridge, MA (US)

(*) Notice: Subject to any disclaimer, the term of this patent is extended or adjusted under 35 U.S.C. 154(b) by 107 days.

This patent is subject to a terminal disclaimer.

(21) Appl. No.: 12/704,990

(22) Filed: Feb. 12, 2010

(65) Prior Publication Data

US 2010/0184145 A1    Jul. 22, 2010

Related U.S. Application Data

(63) Continuation of application No. 11/551,679, filed on Oct. 20, 2006, now Pat. No. 7,700,321.

(60) Provisional application No. 60/728,947, filed on Oct. 21, 2005.

(51) Int. Cl.
C12P 21/08    (2006.01)
(52) U.S. Cl. .................................................. 435/70.21
(58) Field of Classification Search ................ None
See application file for complete search history.

(56) References Cited

U.S. PATENT DOCUMENTS

| | | | |
|---|---|---|---|
| 6,506,559 | B1 | 1/2003 | Driver et al. |
| 6,602,684 | B1 | 8/2003 | Umaña et al. |
| 7,700,321 | B2 | 4/2010 | McPherson et al. |
| 2003/0124653 | A1 | 7/2003 | Canfield |
| 2003/0175969 | A1 | 9/2003 | Beliard et al. |
| 2004/0228856 | A1 | 11/2004 | Presta |
| 2007/0092521 | A1 | 4/2007 | McPherson et al. |

FOREIGN PATENT DOCUMENTS

EP    1176195 A1    1/2002

OTHER PUBLICATIONS

Bosch et al., "The mannosidase inhibitors 1-deoxymannojirimycin and swainsonine have no effect on the biosynthesis and infectivity of Rous sarcoma virus," *Virology* 143:342-346 (1985).
Boyd et al., "The effect of the removal of sialic acid, galactose and total carbohydrate on the functional activity of Campath-1H," *Mol. Immunol.* 32:1311-1318 (1995).
Butters et al. "Novel mannosidase inhibitors probe glycoprotein degradation pathways in cells," *Glycoconj. J.*, Epub., 8 pages (Feb. 21, 2009).
Crispin et al., "Disruption of α-mannosidase processing induces non-canonical hybrid-type glycosylation," *FEBS Letters* 581:1963-1968 (2007).
Crispin et al., "Inhibition of hybrid- and complex-type glycosylation reveals the presence of the GlcNAc transferase I-independent fucosylation pathway," *Glycobiology* 16:748-756 (2006).

Elbein et al., "Kifunensine, a potent inhibitor of the glycoprotein processing mannosidase I," *J. Biol. Chem.* 265:15599-15605 (1990).
Elbein et al., "The pyrrolidine alkaloid, 2,5-dihydroxymethyl-3,4-dihydroxypyrrolidine, inhibits glycoprotein processing," *J. Biol. Chem.* 259(20):12409-12413 (1984).
Fleet et al., "Design synthesis and preliminary evaluation of a potent-mannosidase inhibitor: 1,4-dideoxy-1,4-imino-D-mannitol," *J. Chem. Soc. Chem. Commun.* 1240-1241 (1984).
Gergely et al., "Fc receptors on lymphocytes and K cells," *Biochem. Soc. Trans.* 12(5):739-743 (1984).
Hettkamp et al., "Purification by affinity chromatography of glucosidase I, an endoplasmic reticulum hydrolase involved in the processing of asparagine-linked oligosaccharides," *Eur. J. Biochem.* 142(1):85-90 (1984).
Holliger et al., "Engineered antibody fragments and the rise of single domains," *Nature Biotech.* 23:1126-1136 (2005).
International Search Report for PCT/US2006/060113 dated Aug. 9, 2007.
Kanda et al., "Comparison of biological activity among nonfucosylated therapeutic IgG1 antibodies with three different N-linked Fc oligosaccharides: the high-mannose, hybrid, and complex types," *Glycobiology* 17(1):104-118 (2006).
Kaushal et al., "Selective inhibition of glycoprotein-processing enzymes. Differential inhibition of glucosidases I and II in cell culture," *J. Biol. Chem.* 263(33):17278-17283 (1988).
Ko et al., "Function and glycosylation of plant-derived antiviral monoclonal antibody," *PNAS* 100:8013-8018 (2003).
Köhler et al., "Continuous cultures of fused cells secreting antibody of predefined specificity," *Nature* 256:495-497 (1975).
Kumpel et al., "Galactosylation of human IgG monoclonal anti-D produced by EBV-transformed B-lymphoblastoid cell lines is dependent on culture method and affects Fc receptor-mediated functional activity," *Hum. Antibodies Hybridomas* 5:143-151 (1994).
Legler et al., "Synthesis of 5-amino-5-deoxy-D-mannopyranose and 1,5-dideoxy-1,5-imino-D-mannitol, and inhibition of alpha- and beta-D-mannosidases," *Carbohydr. Res.* 128:61-72 (1984).
Longmore et al., "Product-identification and substrate-specificity studies of the GDP-L-fucose:2-acetamido-2-deoxy-beta-D-glucoside (FUC goes to Asn-linked GlcNAc) 6-alpha-L-fucosyltransferase in a Golgi-rich fraction from porcine liver," *Carbohydrate Res.* 100:365-392 (1982). Lund et al., "Expression and characterization of truncated forms of humanized L243 IgG1. Architectural features can influence synthesis of its oligosaccharide chains and affect superoxide production triggered through human Fcgamma receptor I," *Eur. J. Biochem.* 267:7246-7257 (2000).
Molyneux et al., "Australine, a novel pyrrolizidine alkaloid glucosidase inhibitor from *Castanospermum australe*," *J. Nat. Prod.* 51:1198-1206 (1988).
Nose et al., "Inhibition of Processing of Asparagine-linked Carbohydrate Chains on IgG2a by Using Swainsonine has No Influence Upon Antibody Effector Functions In Vitro," *The J. Immunol.* 145:910-914 (1990).
Palmarzyk et al., "1,4-Dideoxy-1,4-imino-D-mannitol inhibits Glycoprotein Processing and Mannosidase," *Arch. Biochem. Biophys.* 243:35-45 (1985).

(Continued)

*Primary Examiner* — Ilia Ouspenski
(74) *Attorney, Agent, or Firm* — Finnegan, Henderson, Farabow, Garrett & Dunner, LLP

(57) ABSTRACT

Methods for producing antibody-based therapeutics with enhanced ADCC activity are disclosed. The enhanced ADCC activity is attributed to oligomannose-type N-glycans on the antibodies and Fc fusion proteins of the invention. Also disclosed are methods of using such antibody-based therapeutics for targeted killing of cells in a mammal, including therapeutic methods of treating cancers, autoimmune diseases and other diseases.

12 Claims, 28 Drawing Sheets

OTHER PUBLICATIONS

Pan et al., "Castanospermine Inhibits the Processing of the Oligosaccharide Portion of the Influenza Viral Hemagglutinin," *Biochemistry* 22:3975-3984 (1983).

Ravetch et al., "IgG Fc receptors," *Annu. Rev. Immunol.* 9:457-92 (1991).

Rothman et al., "Antibody-Dependent Cytotoxicity Mediated by Natural Killer Cells is Enhanced by Castanospermine-Induced Alterations of IgG Glycosylation," *Mol. Immunol.* 26:1113-1123 (1989).

Sarmay et al., "Ligand inhibition studies on the role of Fc receptors in antibody-dependent cell-mediated cytotoxicity," *Mol. Immunol.* 21:43-51 (1984).

Segal et al., "Bispecific antibodies in cancer therapy," *Curr. Opin. Immunol.* 11:558-562 (1999).

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.* 276:6591-6604 (2001).

Shields et al., "Lack of fucose on human IgG1 N-linked oligosaccharide improves binding to human Fcgamma RIII and antibody-dependent cellular toxicity," *J. Biol. Chem.* 277:26733-26740 (2002).

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.* 278:3466-3473 (2003).

Sondermann et al., "The 3.2-A crystal structure of the human IgG1 Fc fragment-Fc gammaRIII complex," *Nature* 406:267-273 (2000).

Stanley et al., "Chinese hamster ovary cells selected for resistance to the cytotoxicity of phytohemagglutinin are deficient in a UDP-N-acetylglucosamine—glycoprotein N-acetylglucosaminyltransferase activity," *PNAS* 72(9):3323-3327 (1975).

Teillaud, "Engineering of monoclonal antibodies and antibody-based fusion proteins: successes and challenges," *Expert Opin. Biol. Ther.* 5(Suppl. 1):S15-S27 (2005).

Umana et al., "Engineered glycoforms of an antineuroblastoma IgG1 with optimized antibody-dependent cellular cytotoxic activity," *Nature Biotech.* 17:176-180 (1999).

Weikert et al., "Engineering Chinese hamster ovary cells to maximize sialic acid content of recombinant glycoproteins," *Nature Biotech.* 17:1116-1121 (1999).

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells," *J. Immunol.* 160:3393-3402 (1998).

Zhu et al., "Production of human monoclonal antibody in eggs of chimeric chickens," *Nature Biotech.* 23:1159-1169 (2005).

```
         230        240        250        260        270
hIgG1  PAPELLGGPSVFLFPPKPKDTLMISRTPEVTCVVVDVSHEDPEVKFNWYV
hIgG2  PAP-PVAGPSVFLFPPKPKDTLMISRTPEVTCVVVDVSHEDPEVQFNWYV
hIgG3  PAPELLGGPSVFLFPPKPKDTLMISRTPEVTCVVVDVSHEDPEVQFKWYV
hIgG4  PAPEFLGGPSVFLFPPKPKDTLMISRTPEVTCVVVDVSQEDPEVQFNWYV
           ****                                *   * *

280        280        300        310        320
hIgG1  DGVEVHNAKTKPREEQYNSTYRVVSVLTVLHQDWLNGKEYKCKVSNKALP
hIgG2  DGVEVHNAKTKPREEQFNSTFRVVSVLTVVHQDWLNGKEYKCKVSNKGLP
hIgG3  DGVEVHNAKTKPREEQFNSTFRVVSVLTVLHQDWLNGKEYKCKVSNKALP
hIgG4  DGVEVHNAKTKPREEQFNSTYRVVSVLTVLHQDWLNGKEYKCKVSNKGLP 330        340        350        360        370
hIgG1  APIEKTISKAKGQPREPQVYTLPPSREEMTKNQVSLTCLVKGFYPSDIAV
                        D  L
hIgG2  APIEKTISKTKGQPREPQVYTLPPSREEMTKNQVSLTCLVKGFYPSDIAV
hIgG3  APIEKTISKTKGQPREPQVYTLPPSREEMTKNQVSLTCLVKGFYPSDIAV
hIgG4  SSIEKTISKAKGQPREPQVYTLPPSQEEMTKNQVSLTCLVKGFYPSDIAV
       **         *             *

380        390        400        410        420
hIgG1  EWESNGQPENNYKTTPPVLDSDGSFFLYSKLTVDKSRWQQGNVFSCSVMH
hIgG2  EWESNGQPENNYKTTPPMLDSDGSFFLYSKLTVDKSRWQQGNVFSCSVMH
hIgG3  EWESSGQPENNYNTTPPVLDSDGSFFLYSKLTVDKSRWQQGNIFSCSVMH
hIgG4  EWESNGQPENNYKTTPPVLDSDGSFFLYSRLTVDKSRWQEGNVFSCSVMH
           *       *   *                *      *  *

430        440
hIgG1  EALHNHYTQKSLSLSPGK
hIgG2  EALHNHYTQKSLSLSPGK
hIgG3  EALHNRFTQKSLSLSPGK
hIgG4  EALHNHYTQKSLSLSLGK
            **         *
```

FIG. 1C

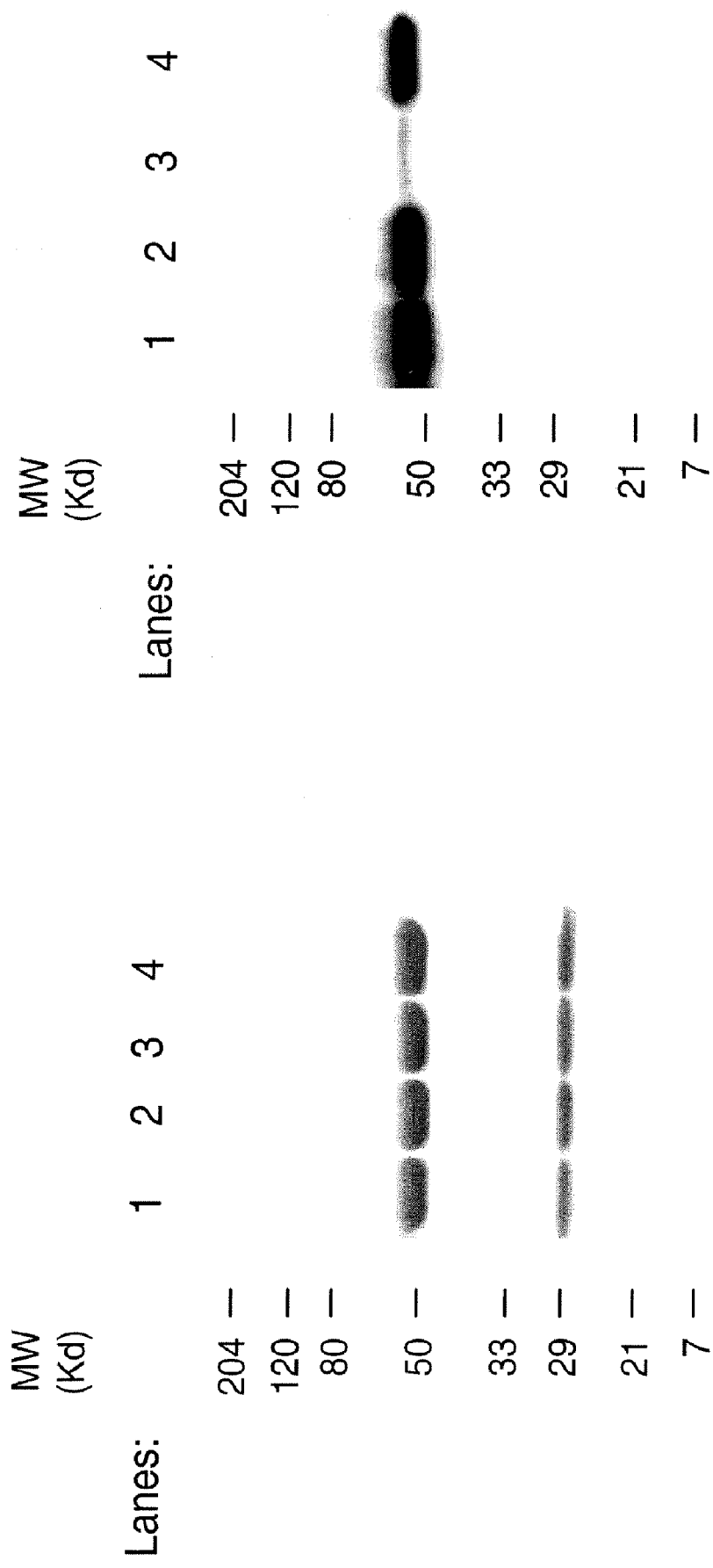

Mass (m/z)

Mass (m/z)

Mass (m/z)

Mass (m/z)

Mass (m/z)

Mass (m/z)

SEQUENCE LISTING

```
<160> NUMBER OF SEQ ID NOS: 4

<210> SEQ ID NO 1
<211> LENGTH: 218
<212> TYPE: PRT
<213> ORGANISM: human
<220> FEATURE:
<221> NAME/KEY: MISC_FEATURE
<222> LOCATION: (127)..(127)
<223> OTHER INFORMATION: D or E
<220> FEATURE:
<221> NAME/KEY: MISC_FEATURE
<222> LOCATION: (129)..(129)
<223> OTHER INFORMATION: L or M

<400> SEQUENCE: 1

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
```

```
            50                  55                  60
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Xaa Glu
        115                 120                 125

Xaa Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 2
<211> LENGTH: 217
<212> TYPE: PRT
<213> ORGANISM: Human

<400> SEQUENCE: 2

Pro Ala Pro Pro Val Ala Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Gln Phe Asn Trp Tyr
         35                  40                  45

Val Asp Gly Val Glu Val His Asn Ala Lys Thr Lys Pro Arg Glu Glu
 50                  55                  60

Gln Phe Asn Ser Thr Phe Arg Val Val Ser Val Leu Thr Val Val His
 65                  70                  75                  80

Gln Asp Trp Leu Asn Gly Lys Glu Tyr Lys Cys Lys Val Ser Asn Lys
             85                  90                  95

Gly Leu Pro Ala Pro Ile Glu Lys Thr Ile Ser Lys Thr Lys Gly Gln
        100                 105                 110

Pro Arg Glu Pro Gln Val Tyr Thr Leu Pro Pro Ser Arg Glu Glu Met
    115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
```

```
                     210                 215

<210> SEQ ID NO 3
<211> LENGTH: 218
<212> TYPE: PRT
<213> ORGANISM: Human

<400> SEQUENCE: 3

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Phe Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 4
<211> LENGTH: 218
<212> TYPE: PRT
<213> ORGANISM: human

<400> SEQUENCE: 4

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110
```

```
Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
    210                 215
```

ANTIBODY-BASED THERAPEUTICS WITH ENHANCED ADCC ACTIVITY

This application is a continuation of Application No. 11/551,679, filed Oct. 20, 2006 now U.S. Pat. No. 7,700,321 (allowed), which claims the benefit of U.S. provisional patent application No. 60/728,947, filed on Oct. 21, 2005, both of which are incorporated by reference.

TECHNICAL FIELD

The technical field of the invention relates generally to protein glycobiology and, more particularly, to antibody engineering and production as well as clinical implications of glycosylation in various antibody-based therapeutics such as, e.g., monoclonal antibodies and Ig fusion proteins.

BACKGROUND OF THE INVENTION

Antibody-based therapeutics, i.e., monoclonal antibodies (mAbs) and Fc fusion proteins, have now "come of age" as therapeutics. There are at least eighteen mAbs and two fusion molecules on the market and more than 150 are currently in clinical trials (see, e.g., Holliger et al. (2005) Nature Biotech., 23:1126-1136 and Theillaud (2005) Expert Opin. Biol. Ther., 5(Suppl. 1):S15-S27). Indications for these therapeutics are varied and include, e.g., organ transplantation (OKT3®, Simulect®, Zenapax®), oncology (Rituxan®, Panorex®, Herceptin®, Mylotarg®, Campath®, Zenapax®, Bexxar®, Erbitux®, Avastin®, HuMax-CD4™), infectious disease (Synagis®), inflammation and autoimmune disease (Humira®, Amevive®, Enbrel®), and allergic asthma (Xolair®). The therapeutic activity of such drugs may be mediated via different mechanisms of action, for example, by inhibiting signaling events in target cells, by direct induction of apoptosis, as well as by indirect immunologic mechanisms, such as antibody-dependent cell-mediated cytotoxicity (ADCC) through binding to Fc receptors and complement-dependent cytotoxicity through binding to C1q (both mechanisms are termed collectively as "effector functions").

Mouse mAbs were first made by Köhler et al. in 1975 (Nature (1975) 256:495-497). The first mAb that was approved for clinical use is a murine antibody (OKT3®). However, the effector functions, immunogenicity, and the pharmacokinetic properties of mouse antibodies (most of them being IgG1 or IgG2a and, in some cases, IgG2b) are generally not satisfactory for therapeutic uses in humans. For example, when mouse antibodies are tested with cells of human origin, the level of ADCC is substantially lower than that with mouse cells. Further studies elucidated that the antibody Fc regions are responsible for effector functions, and that the reduced ADCC is due to a lower binding affinity of murine IgG Fc region to human Fcγ receptors as compared to human antibodies.

Much effort has been made to produce antibody-based therapeutics with decreased immunogenicity and optimized effector functions in humans. As a result, chimeric, humanized and fully human monoclonal antibodies and antibody-based fusion proteins have been developed. Most chimeric and humanized antibodies, as well as antibody-based fusion molecules, contain an Fc region derived from human IgG1, because this subclass exhibits characteristics (FcγRs binding, serum half-life) and functional properties (ADCC, phagocytosis, endocytosis, complement activation) desirable for certain types of immune intervention.

Although some antibody-based therapeutics may function without utilizing antibody effector mechanisms, others may need to recruit the immune system to kill the target cells. If immune system recruitment is desirable for a particular therapeutic, engineering the IgG Fc portion to improve effector function (e.g., improved binding to IgG receptors and/or complement) may be a valuable enhancement.

Several strategies have been explored to enhance immune system recruitment, including: bispecific antibodies, in which one arm of the antibody binds to an Fcγ receptor (see, e.g., Segal et al. (1999) Curr. Opin. Immunol., 11:558-562); cytokine-IgG fusion molecules (e.g., IL-10-Fc, IL-15-Fc); and mutation of amino acid residues responsible for binding to FcγRs (see, e.g., Shields et al. (2001) J. Biol. Chem., 276:6591-6604).

Glycosylation of immunoglobulins can be an essential determinant of effector functions. Therefore, another approach to modify the effector function of a particular IgG is to engineer the glycosylation pattern of the Fc region.

An IgG molecule contains an N-linked oligosaccharide covalently attached at the conserved Asn297 of each of the CH2 domains in the Fc region. The oligosaccharides found in the Fc region of serum IgGs are mostly biantennary glycans of the complex type. Variations of IgG glycosylation patterns include attachment of terminal sialic acid, a third GlcNAc arm (bisecting GlcNAc), a terminal galactosylation, and α-1, 6-linked core fucosylation. Oligosaccharides can contain zero (G0), one (G1), or two (G2) galactoses (see FIG. 1A). The exact pattern of glycosylation depends on the structural properties of IgG subcomponents, in particular, CH2 and CH3 domains (Lund et al. (2000) Eur. J. Biochem., 267:7246-7257). The cell lines used to produce recombinant IgG mAbs or fusion molecules (most often derived from mouse and hamster cell lines) may also influence the synthesis of oligosaccharide chains.

The oligosaccharide moiety of glycoproteins is initially biosynthesized from lipid-linked oligosaccharides to form a $Glc_3Man_9GlcNAc_2$-pyrophosphoryl-dolichol which is then transferred to the protein in the endoplasmic reticulum (ER) (see FIG. 1B). The oligosaccharide portion is then processed in the following sequence. First, all three glucose (Glc) residues are removed by glucosidases I and II to yield $Man_9GlcNAc_2$-protein. The $Man_9GlcNAc_2$ structure may be further processed by the removal of a number of mannose (Man) residues. Initially, four α1,2-linked mannoses are removed to give a $Man_5GlcNAc_2$-protein which is then lengthened by the addition of a N-acetylglucosamine (GlcNAc) residue. This new structure, the $GlcNAcMan_5GlcNAc_2$-protein, is the substrate for mannosidase II which removes the α1,3- and α1,6-linked mannoses. Thereafter, the other sugars, GlcNAc, galactose, and sialic acid, are added sequentially to give the complex types of structures often found on glycoproteins.

Several studies have investigated the relationship between IgG glycoforms and FcγRIII-dependent ADCC.

Galactose—Removal of most of the galactose residues from a humanized mAb IgG1 (Campath®) resulted in reduced complement lysis activity but had no effect on ADCC (Boyd et al. (1995) Mol. Immunol., 32:1311-1318). However, a highly galactosylated form of a human anti-RhD monoclonal IgG is more active in ADCC assays than the agalactosyl form (Kumpel et al. (1994) Antibodies Hybridomas, 5:143-151). Thus, the impact of galactosylation of IgG oligosaccharide on ADCC is controversial.

Static Acid—The terminal sialic acid seems to have no effect on ADCC (Boyd et al. (1995) Mol. Immunol., 32:1311-1318).

N-acetyl-glucosamine—Several studies have focused on the role of bisecting GlcNAc in binding to FcγRIII and ADCC. The glycosylation pattern of a chimeric IgG1 antineuroblastoma antibody has been engineered in CHO cells transfected with β-1,4-N-acetylglucosaminyltransferase III (GnTIII) (Umana et al. (1999) Nature Biotech., 17:176-180; see also U.S. Pat. No. 6,602,684). This enzyme catalyzes the addition of bisecting GlcNAc residue to the N-linked oligosaccharide. The bisecting GlcNAc blocks the α-1,6-linked core fucosylation of N-glycans, since α1,6-fucosyltransferase cannot efficiently use bisecting N-glycans as substrates (Longmore et al. (1982) Carbohydrate Res., 100: 365-392). IgG produced in this cell line exhibited an increased ADCC activity. However, the contribution of bisecting GlcNAc on effector functions as compared to core fucose remains controversial (Shinkawa et al. (2003) J. Biol. Chem., 278:3466-3473).

Fucose—Humanized and chimeric IgG1 mAbs have been produced in a rat hybridoma cell line that expresses a lower level of α-1,6-fucosyltransferase, so that the secreted mAbs have lower fucosylated oligosaccharide than Chinese hamster ovary (CHO)-produced IgG1 (Shinkawa et al. (2003) J. Biol. Chem., 278:3466-3473; see also European Patent Appln. Pub. No. 1176195). These studies have shown that non fucosylated oligosaccharides play a more critical role in enhancing ADCC than bisecting GlcNAc oligosaccharides. This report is consistent with previous studies in which the fucose deficiency of IgG1 had no effect on C1q binding, but provoked an increased binding to human FcγRIIIA and allowed a higher ADCC activity (Shields et al. (2002) J. Biol. Chem., 277: 26733-26740).

Attempts have been made to engineer cell lines that produce recombinant IgG with a well-defined pattern of glycosylation in the Fc region. For example, CHO cell lines expressing high levels of human β-1,4-galactosyltransferase (GT) and/or α-2,3-sialyltransferase (ST) have been made. The structure of IgG oligosaccharides produced in these cells shows a greater homogeneity as compared with control cell lines. Overexpression of GT reduces the amount of terminal GlcNAc, whereas overexpression of ST increases sialylation of oligosaccharides (Weikert et al. (1999) Nature Biotech., 17:116-1121).

There continues to be a need to optimize antibody-based therapeutics, and in particular, to develop methods for producing antibody-based therapeutics with enhanced ADCC activity.

SUMMARY OF THE INVENTION

The invention provides methods of making therapeutic antibodies and Fc fusion proteins with enhanced ADCC activity and methods of using such therapeutics. The invention pertains to antibody-based therapeutics that are fully human, or otherwise contain the Fc domain of human antibodies, e.g., human, humanized or chimeric antibodies and Fc fusion molecules with a human Fc domain or a functional derivative thereof. In preferred embodiments, the Fc domain is from IgG, and more preferably, IgG1.

Antibodies and Fc fusion proteins made by the methods of the invention comprise oligomannose-type N-glycans and are further characterized by one or more of the following properties (as compared to the same antibody or Fc fusion protein containing complex-type N-glycans):
  (a) higher ADCC activity;
  (b) higher binding affinity for FcγRIIIA (and certain other Fcγ receptors);
  (c) similar or higher binding specificity for the target;
  (d) similar or higher binding affinity for the target; and
  (e) similar or lower binding affinity for mannose receptor.

The oligomannose-type N-glycans on the antibodies and Fc fusion molecules of the invention comprise $Man_{5-9}$(GlcNAc)$_2$. Such N-glycans contain no terminal sialic acid, galactose, or GlcNAc. In preferred embodiments, such N-glycans do not contain core fucose. In preferred embodiments, the antibody or Fc fusion protein compositions of the invention contain predominantly $Man_9(GlcNAc)_2$ with diminishing amounts of the oligomannose-type oligosaccharides $Man_8(GlcNAc)_2$, $Man_7(GlcNAc)_2$, $Man_6(GlcNAc)_2$, and $Man_5(GlcNAc)_2$, while containing minor or undetectable amounts of complex-type and/or hybrid type N-glycans.

One method of making an antibody or Fc fusion protein of the invention comprises:
  (a) providing a cell engineered to express the antibody or Fc fusion protein;
  (b) culturing the cell under conditions resulting in secretion of the antibody or Fc fusion protein comprising oligomannose-type N-glycans; and
  (c) recovering the secreted antibody or Fc fusion protein.

Another method of making an antibody of Fc fusion protein of the invention comprises:
  (a) providing a cell engineered to express the antibody or Fc fusion protein;
  (b) culturing the cell under conditions resulting in expression of the antibody or Fc fusion protein comprising oligomannose-type N-glycans; and
  (c) recovering the expressed antibody or Fc fusion protein.

In preferred embodiments, the engineered cell is a mammalian cell, e.g., a CHO cell, a NSO cell, or a mouse hybridoma cell. The engineered cell may be deficient in one or more glycosidases required for early stage processing of N-glycans and/or the culture conditions may be such that the activity of one or more of these glycosidases is inhibited. For example, the cell may be deficient in one or more glycosidases selected from the group consisting of α-glucosidase I, α-glucosidase II, and α-mannosidase I. In addition, or alternatively, the engineered cell may be contacted with an inhibitor of one or more glycosidases selected from the group consisting of α-glucosidase I, α-glucosidase II, and α-mannosidase I. In preferred embodiments, the inhibitor is an inhibitor of α-mannosidase I, e.g., the α-mannosidase I specific inhibitor, kifunensine.

The invention further provides methods of killing a target cell in a mammal by administering a pharmaceutical composition comprising an antibody or Fc fusion protein of the invention to the mammal whereby the antibody mediates the killing of the target cell via ADCC. The methods of killing a target cell include methods of treating diseases in which antibody-directed killing of target cells is desirable, for example, various types of cancers, infectious diseases, and inflammation and autoimmune diseases.

BRIEF DESCRIPTION OF THE FIGURES

FIG. 1C depicts the alignment of native sequences of human IgG Fc domains with differences between the sequences from various IgG isotypes marked with asterisks.

FIG. 2 shows the result of an SDS-PAGE, lectin and antibody blotting of purified TEM mAb A. Aliquots of 5 µg of TEM mAb A samples in reducing sample buffer were applied to each well of a 4-20% SDS-PAGE gel and the gel was stained with Coomassie Blue (FIG. 2A). Lane 1 represents IgG1 from cells treated without any inhibitors; lane 2 represents IgG1 from cells treated with mannostatin A; lane 3 represents IgG1 from cells treated with kifunensine; lane 4 represents IgG1 from cells treated with NB-DNJ. FIG. 2B shows the results of lectin blotting of various antibodies. The proteins (0.5 µg per sample) were separated by SDS-PAGE as described for FIG. 2A, and were transferred to a PVDF membrane. The membrane was blotted with biotinylated lentil lectin and developed with streptavidin-HRP.

" in FIGS. 10A and 10B.

FIG. 17 shows ADCC activity of TEM mAb A from CHO cells treated with various amount of kifunensine.

FIG. 19 shows results from ELISA format assays used to assess binding of various FcγRs to antibody D from cells treated with kifunensine or from untreated cells.

BRIEF DESCRIPTION OF THE SEQUENCES

Figure 1A:
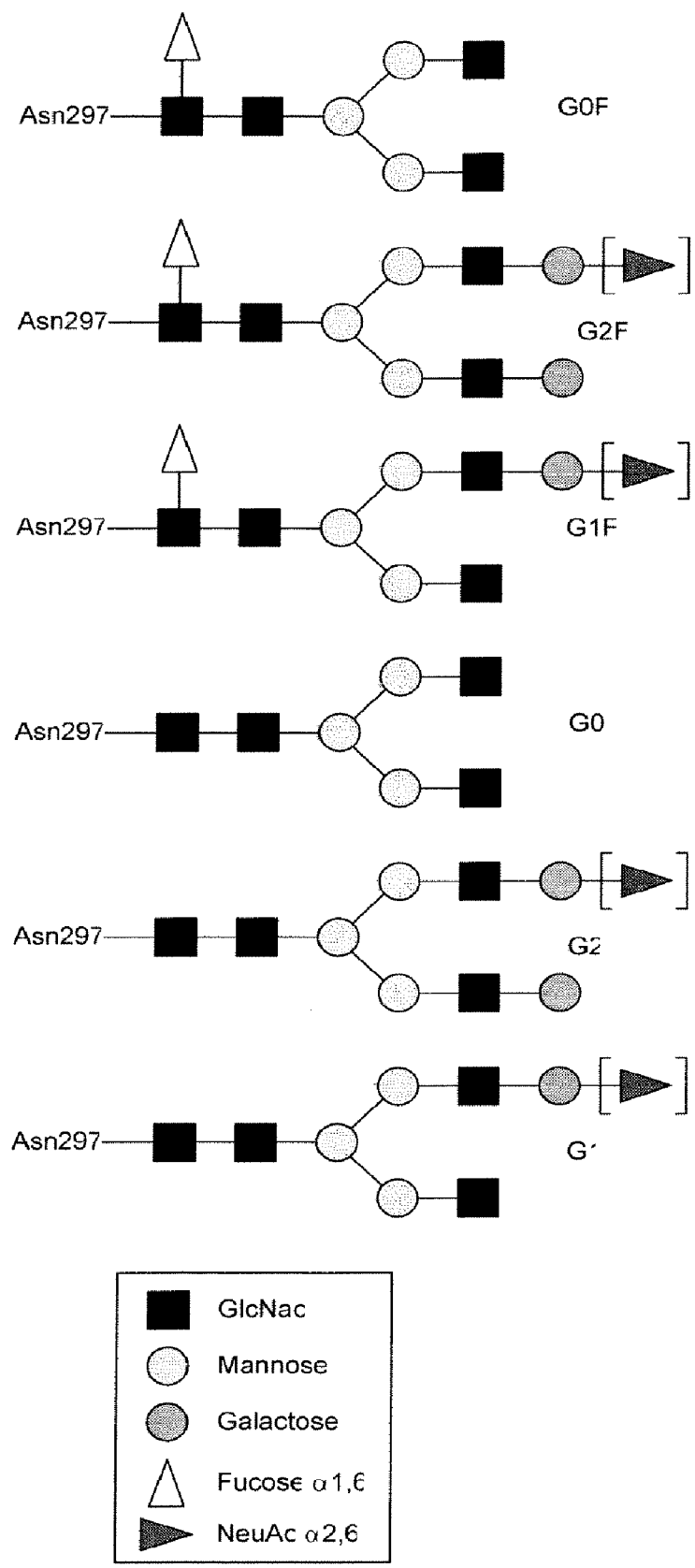
FIG. 1A shows a schematic representation of various glycoforms of IgG. Sugar residues of IgG carbohydrate attached to Asn297 include N-acetylglucosamine (GlcNAc), mannose, galactose, fucose, and sialic acid (NeuAc). The variations in IgG glycoforms depend on the attachment of galactose, NeuAc residues and of bisecting GlcNAc to the core GlcNAc$_2$Man$_3$GlcNAc. N-glycans may contain zero (G0), one (G1) or two (G2) galactose residues, as well as one fucose attached to the first GlcNAc on reducing end (denoted as G0F, G1F, G2F, respectively). However, the major N-glycans found in the recombinant antibodies expressed from most mammalian cell lines are G0F and G1F.
Figure 1B:
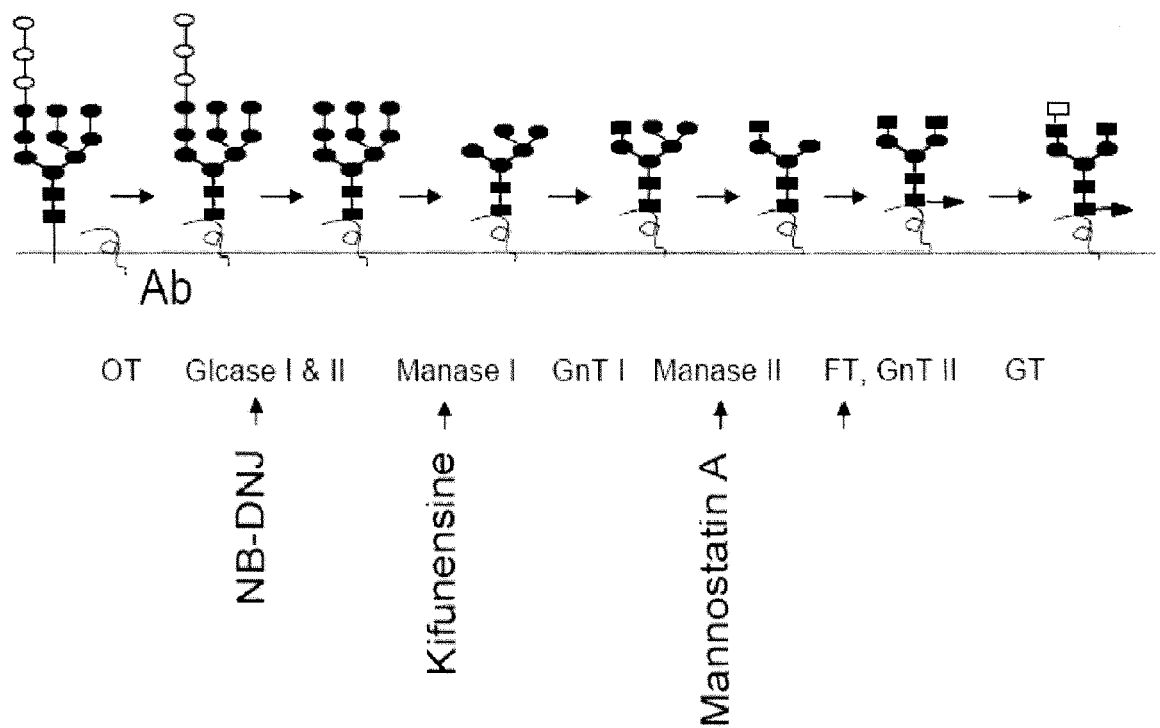
FIG. 1B illustrates the inhibition of the N-linked glycosylation pathway using various inhibitors. The processing of N-glycans on an antibody can be inhibited by inhibitors specific for glycosidases or glycosyltransferases in the lumen of the ER or Golgi. OT denotes oligosaccharyltransferase; Glcase I & II denotes α-glucosidases I and II; Manases I & II denotes α-mannosidases I and II; GnT I & II denotes GlcNAc transferases I and II; FT denotes α-1,6 fucosyltransferase; and GT denotes β-1,4 galactosyltransferase.

SEQ ID NO:1, 2, 3, and 4 are amino acid sequences of the Fc domains from human IgG1, IgG2, IgG3, and IgG4, respectively.

DETAILED DESCRIPTION OF THE INVENTION

In the experiments described in the Examples, CHO and hybridoma cells engineered to express antibodies were cultured in the presence of the α-mannosidase I inhibitor, kifunensine. The treatment of cells with kifunensine resulted in the production of antibodies carrying oligomannose-type N-glycans, while the formation of complex-type N-glycans was blocked. The antibodies carrying oligomannose-type glycans exhibited enhanced ADCC activity as compared to the same antibodies produced without the kifunensine treatment. Thus, antibodies and Fc fusion proteins carrying oligomannose-type N-glycans are useful for various therapies in which Fc-directed killing of target cells is desirable.

Accordingly, the invention provides methods of making therapeutic antibodies and Fc fusion proteins with enhanced ADCC activity, and methods of using such therapeutics.

One method of making an antibody or Fc fusion protein of the invention comprises:
 (a) providing a cell engineered to express the antibody or Fc fusion protein;
 (b) culturing the cell under conditions resulting in secretion of the antibody or Fc fusion protein comprising oligomannose-type N-glycans; and
 (c) recovering the secreted antibody or Fc fusion protein.

Another method of making an antibody of Fc fusion protein of the invention comprises:
 (a) providing a cell engineered to express the antibody or Fc fusion protein;
 (b) culturing the cell under conditions resulting in expression of the antibody or Fc fusion protein comprising oligomannose-type N-glycans; and
 (c) recovering the expressed antibody or Fc fusion protein.

Alternatively, antibodies comprising oligomannose-type N-glycans may be produced by chemical linking of an unglycosylated antibody or Fc fusion protein and a separately synthesized oligosaccharide moiety.

Antibodies and Fc Fusion Proteins

Antibodies belong to the class of proteins known as immunoglobulins. Intact antibodies are typically tetrameric glycosylated proteins composed of two light chains of approximately 25 kDa each and two heavy chains of approximately 50 kDa each. Depending on the amino acid sequence of the constant domain of heavy chains, antibodies can be assigned to five major classes: A, D, E, G, and M, and several of these may be further divided into subclasses (isotypes), e.g., in human: IgG1, IgG2, IgG3, IgG4, IgA1, and IgA2, etc. Heavy and light chains each contain a C-terminal constant region, common to all antibodies of a particular isotype, and an N-terminal variable region that confers binding specificity to the antibody. The term "antibody," as used herein, refers to monoclonal antibodies regardless of their source or method of production, including, e.g., monospecific, polyspecific (e.g., bispecific), humanized, human, chimeric, recombinant, hybrid, mutated, and CDR grafted antibodies. For example, Rituxan®, Simulect®, Remicade®, and Erbitux® are chimeric antibodies; Campath®, Zanapax®, Synagis®, Herceptin®, Mylotarg®, Xolair®, and Avastin® are humanized antibodies; and Humira® and Humax-CD4™ are fully human antibodies. It also includes portions of antibody molecules, such as scFv's, so long as such molecules are linked to an Fc region of an immunoglobulin. The term "polyclonal antibody," as used herein, refers to recombinantly produced polyclonal antibodies. Polycolonal antibodies may be used in the methods and compositions of the invention similarly to other antibodies as described herein.

Routine methods of making antibodies of these various types are well known and are described in, e.g., Antibody Engineering by Borrebaeck (editor), Oxford University Press, 2nd ed., 1995; Antibody Engineering: Methods and Protocols (Methods in Molecular Biology) by Lo (ed.), Humana Press, 2003; and Antibody Engineering (Springer Lab Manuals) by Kontermann et al. (eds.), Springer; 1st ed., 2001.

The terms "Fc domain," "Fc portion," and "Fc region" refer to a C-terminal fragment of a human antibody heavy chain, e.g., from about amino acid (aa) 230 to about aa 447 of γ chain or its counterpart sequence in other types of antibody heavy chains (e.g., α, δ, ε and µ for human antibodies), or a naturally occurring allotype thereof. Unless otherwise specified, the commonly accepted Kabat amino acid numbering for immunoglublins is used throughout this disclosure (see Kabat et al. (1991) Sequences of Protein of Immunological Interest, 5th ed., United States Public Health Service, National Institute of Health, Bethesda, Md.). The terms "non-human Fc domain," "non-human Fc portion," and "non-human Fc region" refer to the corresponding C-terminal fragment of a non-human antibody heavy chain (e.g., from mouse, rat, goat, or rabbit). Non-human Fc domains can be used in the methods and compositions of the invention similarly to human Fc domains as described herein.

FIG. 1C illustrates an alignment of human Fc domains from IgG1 (SEQ ID NO:1), IgG2 (SEQ ID NO:2), IgG3 (SEQ ID NO:3), and IgG4 (SEQ ID NO:4). The alignment shows about 91-94% identity among these Fc domains. A comparison of the human Fc domains to mouse Fc domains from IgG1, IgG2A, IgG2B, and IgG3 reveals identity of about 61-68%.

Immunoglobulin G (IgG) Fc receptors (FcγRs) mediate the cellular effector function of IgG antibodies. A subset of amino acid residues in the Fc region are involved in the binding to FcγRs. It has been demonstrated that amino acid sequence variants that exhibit increased binding to FcγRIII also possess enhanced ADCC activity (Shields et al. (2001) J. Biol. Chem., 276:6591-6604). For human FcγRIIIA, this subset includes, for example, the following: (1) Lys274-Arg301 and Tyr407-Arg416 (Sarmay et al. (1984) Mol. Immunol., 21:43-51 and Gergely et al. (1984) Biochem. Soc. Trans., 12: 739-743); (2) Leu234-Ser239, Asp265-Glu269, Asn297-Thr299, and Ala327-Ile332 (Sondermann et al. (2000)

Nature, 406:267-273, and (3) T256, K290, S298, E333, K334, A339 (Shields et al. (2001) J. Biol. Chem., 276:6591-6604; see also variants disclosed in U.S. Patent Application No. 2004/0228856). For example, Fc variants T256A, K290A, S298A, E333A, K334A, A339T have been described as having enhanced ADCC activity as compared to native sequences (see, e.g., Shields, supra). Furthermore, a number of amino acids can be mutated without any loss of ADCC function.

Accordingly, engineered Fc domains may contain only a partial or a mutated amino acid sequence of the naturally occurring Fc domains, e.g., as specified above. Therefore, for the purposes of the present disclosure, the terms "Fc domain" and its cognates refer not only to the naturally occurring forms but also to engineered Fc domains. For example, an Fc domain may comprise a sequence, which is at least 80%, 85%, 90%, 95%, or 100% identical to SEQ ID NO:n over the entire length of SEQ ID NO:n, wherein n=1, 2, 3, or 4.

In the methods of the invention, antibody-based therapeutics are fully human, or otherwise contain the Fc domain of human antibodies, e.g., humanized or chimeric antibodies and Fc fusion molecules with a human Fc domain or a functional derivative thereof (e.g., a derivative that binds to one or more Fc receptors, e.g., FcγRIIIA). The derivatives include, for example, native sequences in which conservative substitutions were made and/or nonessential amino acids were deleted.

In preferred embodiments, the antibodies or the Fc portion is derived from IgG1. However, the invention can also be practiced with other classes of antibodies, including IgG, IgA, IgD, IgE and IgM, and isotypes, such as, e.g., IgG1, IgG2, IgG3, IgG4, IgA1, and IgA2. For example, IgG4 has limited capacity to activate effector functions, while IgAs are potent activators of ADCC. In either instance, the ADCC activity of the antibodies or the Fc fusion molecules can be enhanced using methods of the invention.

The specificity of the antibody toward its antigen or the specificity of the non-Fc portion of an Fc fusion protein for its target will vary depending on the requirements of a particular application. For example, Enbrel® contains a receptor-binding domain of a TNF receptor (p75), and Amevive® contains a CD2-binding domain of LFA-3, each fused to a human Fc domain. For example, the Fc domain may be linked to an enzyme, a toxin, a growth factor, a chemokine, or cytokine. Further, Fc fusion proteins may contain an antibody hinge region and/or a linker.

Cells and Culture Conditions

In some methods of the invention, a cell engineered to express an antibody or Fc fusion is provided. In preferred embodiments, the engineered cell is propagated in cell culture (e.g., as opposed to being a part of a living animal ("in vivo")). For example, the cell may be a mammalian cell, e.g., a CHO cell or a human cell or a mouse hybridoma cell. Examples of other types of cells that may be used for expression of antibodies and Fc fusion proteins include mouse myeloma cells (e.g., NSO), human embryonic kidney cells (e.g., HEK293), monkey kidney cells (e.g., COS), human epithelial carcinoma cells (e.g., HeLa), human fibrosarcoma cells (e.g., HT-1080), baby hamster kidney cells, yeast cells, insect cells, and others (see, e.g., Fernandez et al. (eds.) Gene Expression Systems, Academic Press, 1999). Any cell compatible with the present invention and appropriate culture conditions may be used.

The engineered cell may be deficient in one or more glycosidases required for early stage processing of N-glycans and/or the culture conditions may be such that the activity of one or more of these glycosidases is inhibited. As a result of one or both of these conditions, oligosaccharide synthesis is shifted toward oligomannose-type species.

For example, the cell may be deficient in one or more glycosidases selected from the group consisting of α-glucosidase I, α-glucosidase II, and α-mannosidase I. Cells deficient in a glycosidase of interest can be engineered using methods as described, e.g., in Tymms et al. (eds.) Gene Knockout Protocols (Methods in Molecular Biology), Humana Press, 1st ed., 2001; and in Joyner (ed.) Gene Targeting: A Practical Approach, Oxford University Press, 2nd ed., 2000. For instance, glycosidase-deficient cells can be engineered using lectin selection as described in Stanley et al. (1975) Biochemistry, 72(9):3323-3327.

In addition, or alternatively, the engineered cell may be contacted with an inhibitor of one or more glycosidases selected from the group consisting of α-glucosidase I, α-glucosidase II, and α-mannosidase I. Inhibitors of these enzymes may be, for example, small molecules or small interfering RNAs (siRNAs).

siRNAs are short (20-25 nt) double stranded RNAs that inhibit a glycosidase of interest via post-transcriptional gene silencing. A glycosidase-specific siRNA may be prepared and used as described in U.S. Pat. No. 6,506,559 and/or using other suitable methods (see, e.g., Appasani (ed.) RNA Interference Technology From Basic Science to Drug Development, Cambridge University Press, 1st ed., 2005; and Uei-Ti et al. (2004) Nucleic Acids Res., 32(3):936-948).

Examples of small molecule α-glucosidase I inhibitors include castanospermine (Pan et al. (1983) Biochemistry, 22:3975-3984, deoxynojirimycin (DNJ; Hettkamp et al. (1984) Eur. J. Biochem., 142:85-90) and N-alkyl and N-alkenyl derivatives thereof (e.g., N-butyl-DNJ); 2,5-dihydromethil-3,4-dihydroxypyrrolidine (DMDP; Elbein et al. (1984) J. Biol. Chem., 259:12409-12413); and australine (Molyneux et al. (1988) J. Nat. Prod., 51:1198-1206).

Examples of small molecule α-glucosidase II inhibitors include DNJ and N-alkyl and N-alkenyl derivatives thereof; and MDL 25637 (Hettkamp et al. (1984) Eur. J. Biochem., 142: 85-90; Kaushal et al. (1988) J. Biol. Chem., 263: 17278-17283).

Examples of small molecule α-mannosidase I inhibitors include deoxymannojirimycin (DMJ; Legler et al. (1984) Carbohydr. Res., 128:61-72) and derivatives thereof (e.g., N-methyl derivative as described in Bosch et al. (1985) Virology, 143:342-346), 1,4-dideoxy-1,4-imino-D-mannitol (DIM; Fleet et al. (1984) J. Chem. Soc. Chem. Commun., 1240-1241 and Palmarzyk et al. (1985) Arch. Biochem. Biophys., 243:35-45), and kifunensine (Elbein (1990) J. Biol. Chem., 265:15599-15605).

In preferred embodiments, the engineered cells are cultured in the presence of the α-mannosidase I inhibitor, kifunensine. In certain embodiments, kifunensine may be used at a concentration of 0.01 to 100 μg/ml, 0.01 to 75 μg/ml, 0.01 to 50 μg/ml 0.01 to 40 μg/ml, 0.01 to 30 μg/ml, 0.01 to 20 μg/ml, 0.1 to 10 μg/ml, 0.1 to 2.0 μg/ml, or 1 to 0.5 μg/ml for a period of at least 12, 24, 48, 72 hours or 4, 7, 10, 20 days or longer, or continuously. In nonlimiting illustrative embodiments, CHO or hybridoma cells are incubated with about 0.5-10 μg/ml kifunensine for over 10 days.

Characteristics of Antibodies Produced

Antibodies and Fc fusion proteins made by the methods of the invention comprise oligomannose-type N-glycans and are further characterized by one or more of the following properties (vis-à-vis the same antibody or Fc fusion protein with complex-type N-glycans ("wild-type")):

(a) higher ADCC activity;
(b) higher binding affinity for FcγRIIIA (and certain other Fcγ receptors);
(c) substantially same or better binding specificity for the target;
(d) substantially same or higher binding affinity for the target; and
(e) substantially same or lower binding affinity for mannose receptor.

"ADCC activity" refers to the ability of an antibody or Fc fusion protein to elicit an ADCC reaction. ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell. The primary mediator cells are natural killer (NK) cells. NK cells express FcγRIII only, with FcγRIIIA being an activating receptor and FcγRIIIB an inhibiting one; monocytes express FcγRI, FcγRII and FcγRIII (Ravetch et al. (1991) Annu. Rev. Immunol., 9:457-92). ADCC activity can be assessed directly using an in vitro assay, e.g., a $^{51}$Cr release assay using peripheral blood mononuclear cells (PBMC) and/or NK effector cells as described in the Examples and Shields et al. (2001) J. Biol. Chem., 276: 6591-6604, or another suitable method. ADCC activity may be expressed as a concentration of antibody or Fc fusion protein at which the lysis of target cells is half-maximal. Accordingly, in some embodiments, the concentration of an antibody or Fc fusion protein of the invention, at which the lysis level is the same as the half-maximal lysis level by the wild-type control, is at least 2-, 3-, 5-, 10-, 20-, 50-, 100-fold lower than the concentration of the wild-type control itself. Additionally, in some embodiments, such as, e.g., TEM mAb A, the antibody or Fc fusion protein of the invention may exhibit a higher maximal target cell lysis as compared to the wild-type control. For example, the maximal target cell lysis of an antibody or Fc fusion protein of the invention may be 10%, 15%, 20%, 25% or more higher than that of the wild-type control.

The binding affinity of an antibody or Fc fusion protein to its target as well as to Fc receptors and mannose receptors may be assessed using surface plasmon resonance as described in the Examples and/or ELISA as described in Shields et al. (2001) J. Biol. Chem., 276:6591-6604 or other suitable method. In some embodiments, the binding constant $K_d$ of an antibody or Fc fusion protein for FcγRIIIA may be above that of the wild-type control by at least 2-, 5-, 10-, 50-fold, or higher. The binding constant $K_d$ of an antibody or Fc fusion protein of the invention for its target (e.g., antigen) may be substantially the same (i.e., ±50%) as the wild-type control or above it. In some embodiments, the binding constant $K_d$ of an antibody or Fc fusion protein of the invention for mannose receptors may be substantially the same (i.e., ±50%) as the wild-type control or below it.

In some embodiments, certain pharmacokinetic parameters of an antibody or Fc fusion protein of the invention are same or better that those of wild-type control. For example, in some embodiments, elimination half-life ($t_{1/2}$) and/or the area under the concentration curve (AUC) may be substantially the same (i.e., ±50%) as the wild-type control or above it. Pharmacokinetic parameters can be measured in humans or using an appropriate animal model (e.g., as described the Examples) or other methods (see, e.g., Shargel et al. (1995) Applied Biopharmaceutics and Pharmacokinetics, 4th ed., McGraw-Hill/Appleton).

The binding specificity of an antibody or Fc fusion protein can be determined by, e.g., flow cytometry as described in the Examples, Western blotting, or another suitable method. In some embodiments, an antibody or Fc fusion protein of the invention is directed against a human target protein (a human antigen in case of an antibody) expressed on the surface of a target cell. In some embodiments, it may be directed against a soluble antigen. In some other embodiments, an antibody or Fc fusion protein of the invention is directed against a pathogenic target (e.g., viral or bacterial protein). The antibody or Fc fusion protein may be either specific to a human target or may cross-react with corresponding targets from other species.

The oligomannose-type N-glycans on the antibodies and Fc fusion molecules of the invention comprise one or more oligomannose-type oligosaccharides selected from the group consisting of $Man_9(GlcNAc)_2$, $Man_8(GlcNAc)_2$, $Man_7(GlcNAc)_2$, $Man_6(GlcNAc)_2$, and $Man_5(GlcNAc)_2$.

Accordingly, in preferred embodiments, the antibody and Fc fusion protein compositions of the invention contain predominantly $Man_9(GlcNAc)_2$ with diminishing or undetectable amounts of the oligomannose-type N-glycans $Man_8(GlcNAc)_2$, $Man_7(GlcNAc)_2$, $Man_6(GlcNAc)_2$, and $Man_5(GlcNAc)_2$, while containing minor (e.g., less than 10% relative to all N-glycans) or undetectable amounts of complex type N-glycans (such as, e.g., G0, C1, G2, G0F, G1F, G2F, and G0F-Gn).

In some embodiments, compositions produced by the methods of the invention contain at least 20%, 30%, 40%, 50%, 60%, 70%, 90% or more (by molar ratio relative to all N-glycans) oligomannose-type glycans $Man_{5-9}(GlcNAc)_2$. In some embodiments, the $Man_{5-9}(GlcNAc)_2$ in the compositions of the invention are substantially unfucosylated, i.e., they contain less than 30%, 25%, 20%, 15%, 10%, 5%, 1% (by molar ratio, relative to all N-glycans) or less fucose. In some embodiments, the compositions contain less than 30%, 20%, 10%, 5%, 1% (by molar ratio, relative to all N-glycans) or less $Man_5(GlcNAc)_2$ and/or $Man_6(GlcNAc)_2$ glycans. In some embodiments, the compositions contain minor (i.e., less than 10% by molar ratio relative to all N-glycans) or undetectable amounts of $Man_4(GlcNAc)_2$. In some embodiments, the compositions contain less than 80%, 70%, 60%, 50%, 40%, 30%, 20%, 10%, 5%, 1% (by molar ratio, relative to all N-glycans) or less complex-type glycans.

Glycan composition can be assessed using, e.g., lectin blotting, HPLC and/or mass spectrometry analysis as described in the Examples and/or other methods as described in, e.g., Townsend et al. (1997) Techniques in Glybiology, CRC Press.

Uses

The invention further provides methods of killing a target cell in a mammal, comprising administering an antibody or Fc fusion protein of the invention to the mammal whereby the antibody mediates the killing of the target cell via ADCC. The target cell in the methods of the invention may be a cancerous cell, an infected cell, a cell of the immune system (e.g., a B cell or a T cell), or any other cell for which cell killing is desired. The mammal to whom the antibody or Fc fusion protein is administered may be a human, or of another species, e.g., a rodent.

The methods of killing a target cell include methods of treating diseases in which antibody-directed killing of target cells is desirable, by administering a pharmaceutical composition comprising an antibody or Fc fusion protein of the invention to a mammal. In addition to the antibody or Fc fusion protein, the pharmaceutical compositions comprise a pharmaceutically acceptable excipient. The formulation of pharmaceutical compositions varies depending on the intended route of administration, the biological activity of the active ingredient and other parameters (see, e.g., by Rowe et al. (2003) Handbook of Pharmaceutical Excipients, 4th ed., APhA Publications.)

Antibody-based therapeutics of the invention are broadly applicable to any disease or condition in which antibody-directed killing of target cells is desirable. Diseases and conditions to be treated with compositions of the invention include various types of cancers, infectious diseases, inflammatory and immune-mediated diseases (including autoimmune diseases), renal diseases, transplantation (e.g., stem cell or organ transplantation), etc.

Examples of cancers that may be amenable to treatment with compositions of the invention include, without limitation, leukemias, lymphomas, myelomas and other cancers of hematopoietic origin, melanomas and other cancers of the skin, and cancers of the kidney, breast, lung, bone, colon, rectum, uterus, cervix, ovaries, pancreas, prostate, testes, bladder, stomach, brain, and thyroid. Additional cancers include those listed in Table 1 of U.S. Pat. No. 6,359,193.

Examples of infectious diseases that may be amenable to treatment with compositions of the invention include viral infections (e.g., RSV, HCV, and West Nile virus).

Examples of inflammatory and immune-mediated diseases that may be amenable to treatment with compositions of the invention include rheumatoid arthritis (RA), psoriasis, systemic lupus erythematosus (SLE) and lupus nephritis, insulin-dependent diabetes mellitus (IDDM; type I diabetes), inflammatory bowel disease (IBD), graft-versus-host disease (GVHD), celiac disease, autoimmune thyroid disease, Sjögren's syndrome, autoimmune gastritis, autoimmune hepatitis, cutaneous autoimmune diseases, autoimmune dilated cardiomyopathy, myocarditis, multiple sclerosis (MS), myasthenia gravis (MG), vasculitis (e.g., Takayasu's arteritis and Wegener's granulomatosis), autoimmune diseases of the muscle, autoimmune diseases of the testis, autoimmune ovarian disease, and autoimmune uveitis.

Additional disorders that may be amenable to treatment with compositions of the invention include fibrosis (e.g., kidney fibrosis), Addison's disease, Syndenham's chorea, ulcerative colitis, polymyalgia, pernicious anemia, and pernicious anemia.

"Administration" is not limited to any particular delivery system and may include parenteral (including subcutaneous, intravenous, intramedullary, intraarticular, intramuscular, or intraperitoneal injection), topical, transdermal, and oral. Administration may occur in a single dose or in repeat administrations. The antibodies and Fc fusion proteins may be administered in combination with other therapeutic agents. For example, in treating cancers, antibodies and Fc fusion proteins may be combined with chemotherapeutic agents (see, e.g., PCT Application Pub. No. WO 2005/050200), radiation and other treatments (see, e.g., Schwartz et al. (ed.) Combination Cancer Therapy: Modulators and Potentiators, Humana Press, 2005).

Most commonly, antibodies and Fc fusion proteins are administered in an outpatient setting by weekly administration at 0.1-50 mg/kg, e.g., 1-10 µg/kg, doses by slow intravenous (IV) infusion. The appropriate therapeutically effective dose, routes of administration and regimens will be determined by a physician based on the biological activity of the particular antibody in question; exemplary doses for marketed antibodies can be found in 2005 Physicians' Desk Reference (PDR) Thomson Healthcare, 59th ed., 2004; and Remington: The Science and Practice of Pharmacy, eds. Gennado et al., 20th ed, Lippincott, Williams & Wilkins, 2000.

The following Examples provide illustrative embodiments of the invention. The Examples do not in any way limit the invention.

EXAMPLES

Example 1

Treatment of Cells and Purification of Antibodies

Hybridoma cells expressing TEM mAb A, an antibody against a tumor vascular associated antigen, were grown in medium containing 1% fetal bovine serum with low IgG (Invitrogen Corp.), 5 µg/ml bovine insulin, 5 µg/ml human transferrin, 0.01 mM ethanolamine and 25 nM sodium selenite. Cells were treated once with the following inhibitors: 20 µg/ml mannostatin A, and 0.5 mM NB-DNJ for 4 days; and twice with 2 µg/ml kifunensine at days 0 and 2; or cultured without inhibitors ("control").

Figure 2C:
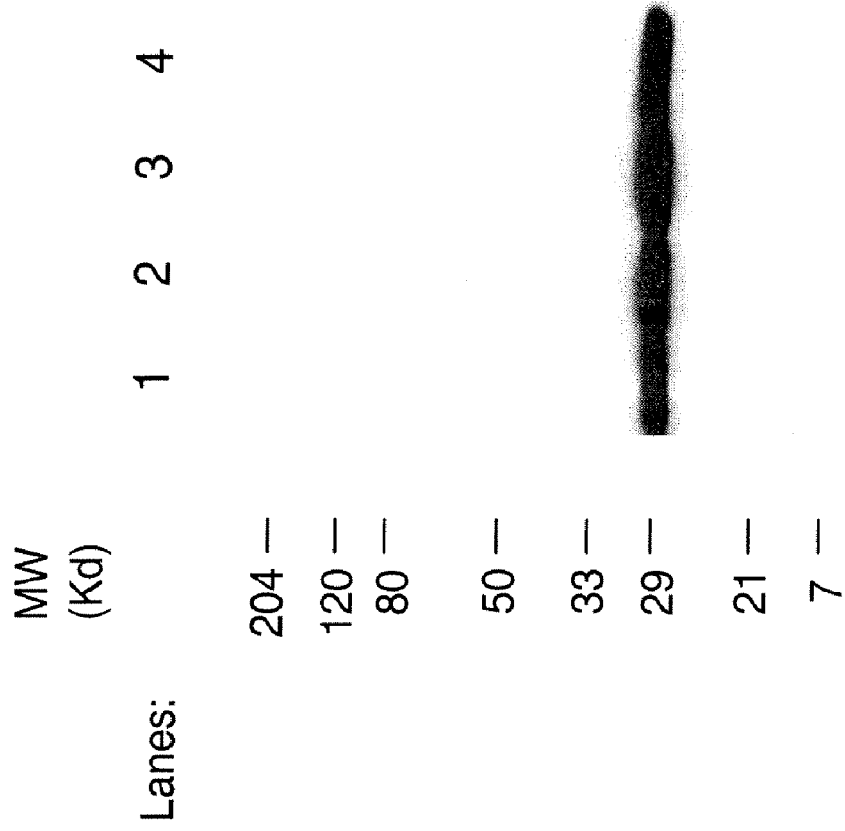
FIG. 2C shows the same membrane as in FIG. 2B that stripped and re-blotted using anti-human Fab antibody conjugated with HRP.

CHO cells expressing TEM mAb B, a different antibody against a tumor vascular associated antigen, were grown in CD-CHO media with 4 mM glutamine. Cells were cultured for three days, while being treated with 2 µg/ml kifunensine at days 0 and 2 or cultured without kifunensine ("control"). Antibodies in the media were purified using a Protein A Sepharose™ column. After loading the column, the column was washed extensively with 15 column volumes of PBS buffer, pH 7.1, or HEPES buffer, pH 8.0, and the antibodies were eluted with 50 mM sodium succinate buffer, pH 3.0 or pH 3.75. The eluates were collected in tubes at 1 ml per fraction with 1 M Tris buffer, pH 8.0. The purified antibodies were buffer-exchanged into PBS buffer, pH 7.2, and the protein concentration was determined using A280. The purity of antibodies was evaluated on a 4-20% SDS-PAGE and stained with Coomassie blue. More than 90% purity was observed for TEM mAb A (FIG. 2A). Similar results were obtained for TEM mAb B.

Example 2

Lectin Blotting

Antibody samples purified as described in Example 1 were resolved on a 4-20% SDS-PAGE and transferred to a PVDF membrane. The membrane was incubated one hour with biotinylated lentil lectin (a lectin specific for α-1,6 linked fucose) in 50 mM Tris buffer, pH 7.4, containing 0.5 M NaCl, 1 mM CaCl$_2$, 1 mM MgCl$_2$, 1% BSA and 0.5% Tween 20. Thereafter, the membrane was washed and incubated with streptavidin-HRP in the same buffer and then developed using a chemoluminescent reagent.

The results for TEM mAb A are shown in FIG. 2B. The results indicate that the antibody from cells treated with kifunensine contained significantly less N-glycans with α-1,6-linked fucosylated structures. (Similar results were observed for TEM mAb B samples.)

The same membrane was stripped using stripping buffer (Pierce), incubated with an anti-human Fab-HRP antibody and developed using a chemoluminescent reagent. The results (FIG. 2C) confirmed equal loading of the antibody samples.

Example 3

MALDI-TOF Mass Spectrum Analysis of Oligosaccharides

N-linked glycans from antibodies purified as described in Example 1 were released with PNGase F. After filtration through 10 kDa filters, the filtrates were treated with Dowex AG-50 (H⁺), AG501, and 018 ziptip sequentially. Aliquots of samples were applied to a target, followed by sDHB matrix. The MALDI-TOF mass spectra were acquired using a Voyager-DE PRO Biospectrometry Workstation (Applied Biosystems, Foster City, Calif., USA) in the positive-ion and reflective mode.

The results from the analysis of TEM mAb A, as described in Example 1, are shown in FIG. 3 and Table 1.

TABLE 1

| Groups | Observed$^a$ m/z | Theoretical$^a$ m/z | Structures |
|---|---|---|---|
| Control | 1485.9867 (peak 1) | 1485.5344 | (HexNAc)$_2$(Deoxyhexose)$_1$ + (Man)$_3$(GlcNAc)$_2$ G0F |
|  | 1648.1070 (peak 2) | 1647.5874 | (Hex)$_1$(HexNAc)$_2$(Deoxyhexose)$_1$ + (Man)$_3$(GlcNAc)$_2$ G1F |
| Mannostatin treatment | 1486.0117 (peak 1) | 1485.5344 | (HexNAc)$_2$(Deoxyhexose)$_1$ + (Man)$_3$(GlcNAc)$_2$ G0F |
|  | 1648.1381 (peak 2) | 1647.5874 | (Hex)$_1$(HexNAc)$_2$(Deoxyhexose)$_1$ + (Man)$_3$(GlcNAc)$_2$ G1F |
| Kifunensine treatment | 1743.9953 (peak 1) | 1743.5814 | (Hex)$_5$ + (Man)$_3$(GlcNAc)$_2$ Man8 without fucose |
|  | 1906.1454 (peak 2) | 1905.6344 | (Hex)$_6$ + (Man)$_3$(GlcNAc)$_2$ Man9 without fucose |
| NB-DNJ treatment | 1485.9195 (peak 1) | 1485.5344 | (HexNAc)$_2$(Deoxyhexose)$_1$ + (Man)$_3$(GlcNAc)$_2$ G0F |
|  | 1648.0156 (peak 2) | 1647.5874 | (Hex)$_1$(HexNAc)$_2$(Deoxyhexose)$_1$ + (Man)$_3$(GlcNAc)$_2$ G1F |
|  | 2068.2641 (peak 3) | 2067.6874 | (Hex)$_7$ + (Man)$_3$(GlcNAc)$_2$ Man9 containing one glucose without fucose |

$^a$m/z values are for the [M + Na]⁺ ions.

Figure 3A:
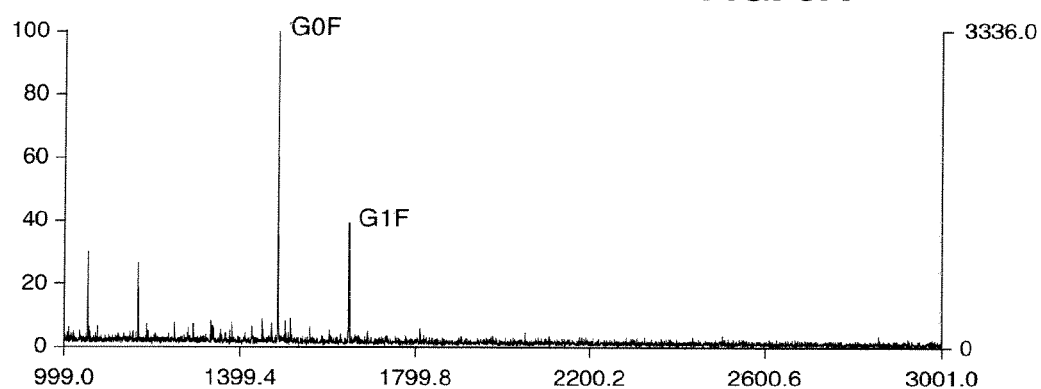
FIG. 3 shows results of a MALDI-TOF mass spectrometry analysis of carbohydrates from TEM antibodies. Carbohydrates on TEM mAb A from cells treated without inhibitor (A), with mannostatin A (B), kifunensine (C) and NB-DNJ (D) and carbohydrates on TEM mAb B from cells treated without inhibitor (E) and with kifunensine (F) were analyzed using MALDI-TOF MS analysis.
Figure 3B:
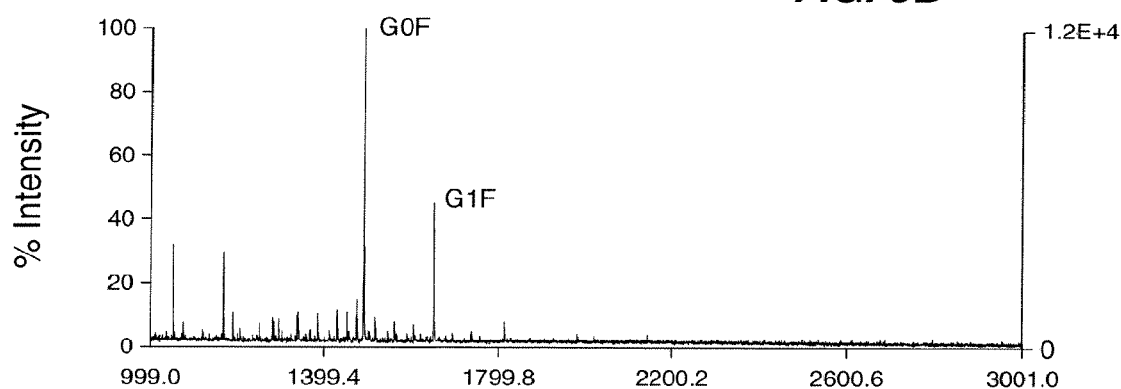
Figure 3C:
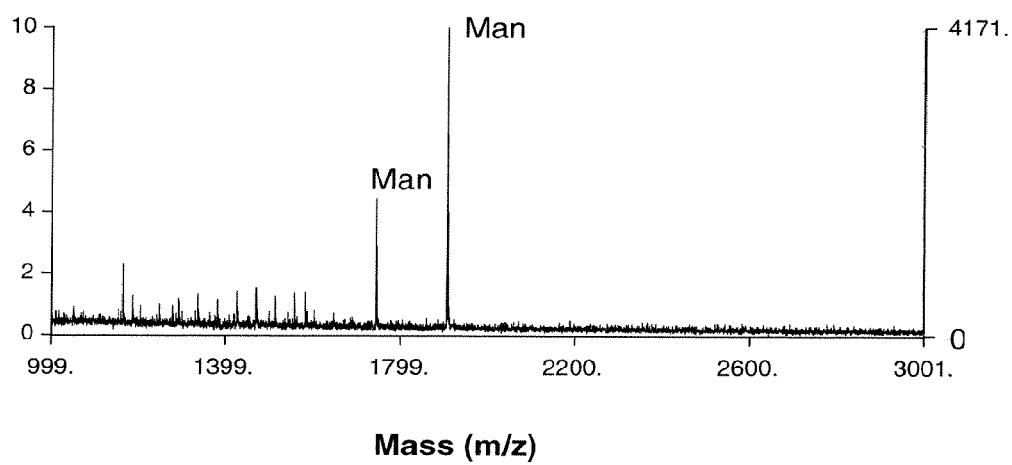
Figure 3D:
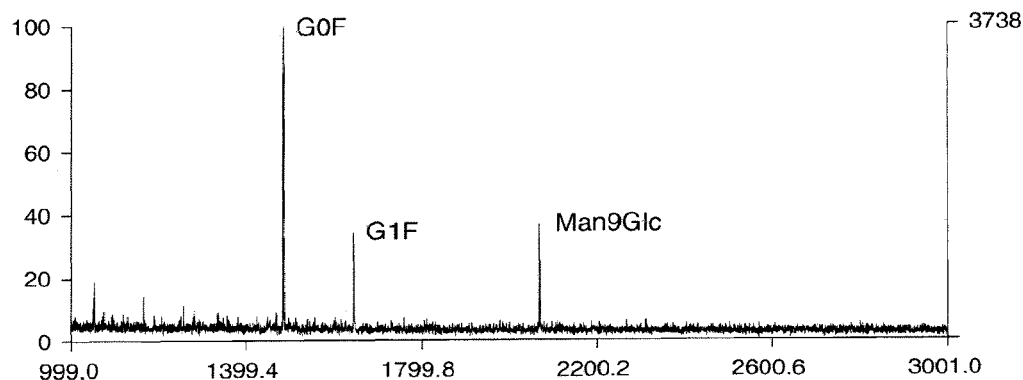
Figure 3E:
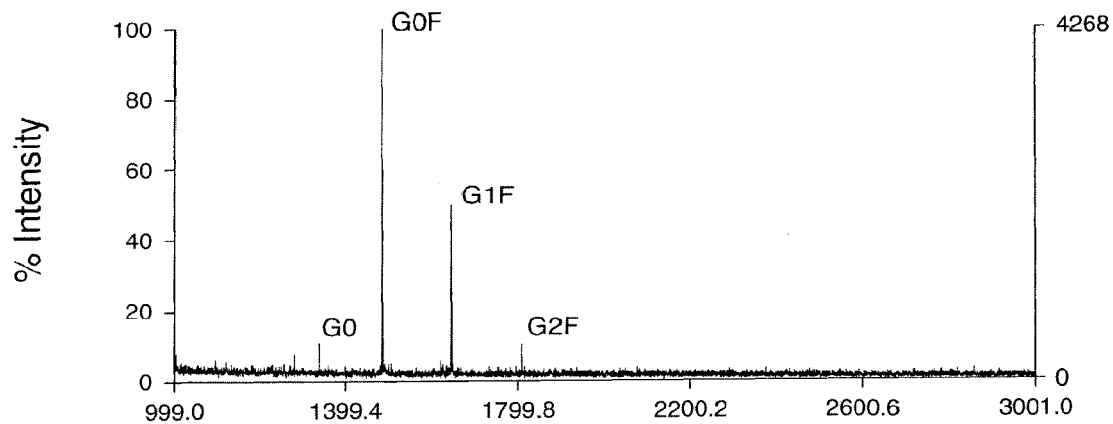
Figure 3F:
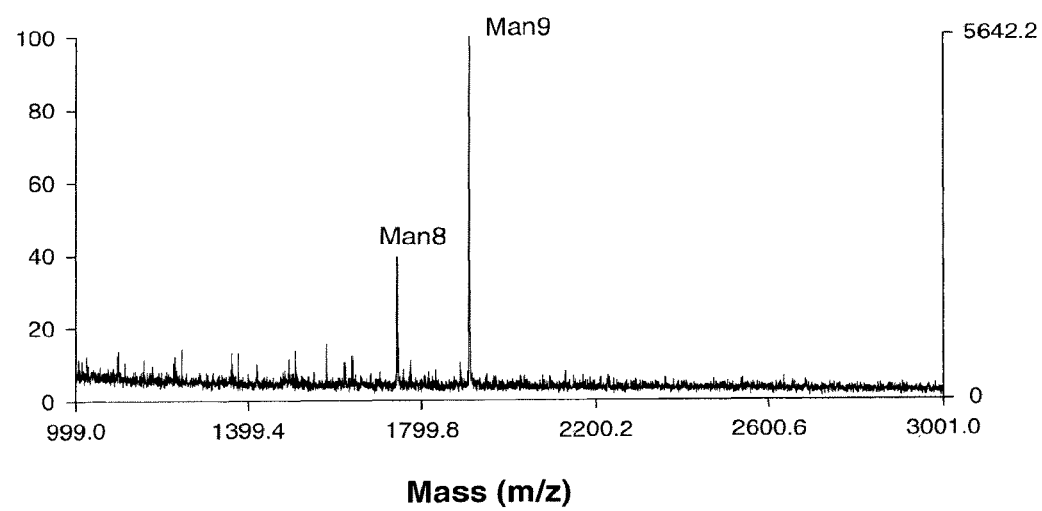

The data indicate that TEM antibodies from cells treated with kifunensine contained mainly Man$_9$GlcNAc$_2$ (Man9), Man$_9$GlcNAc$_2$ (Man8) and Man$_7$GlcNAc$_2$(Man7) without fucose as major N-glycans (FIGS. 3C and 3F) while the major N-glycans in the same antibodies from control cells were fucosylated biantennary species with 0 or 1 galactose, including GlcNAc$_2$Man$_3$GlcNAc$_2$Fuc$_1$ (G0F) and Gal$_1$GlcNAc$_2$Man$_3$GlcNAc$_2$Fuc$_1$ (G1F) (FIGS. 3A and 3E). The carbohydrates in TEM mAb A from cells treated with mannostatin A were similar to those found in control antibody (FIG. 3B). However, there were significant amounts of Glc$_1$Man$_9$GlcGNAc$_2$ (Man9Glc) in TEM mAb A from cells treated with NB-DNJ (FIG. 3D). The data indicate that kifunensine is more effective in blocking the glycosylation to complex-type structures than NB-DNJ. No alteration in glycosylation occurred in the antibody expressed in cells treated with mannostatin A.

Example 4

HPLC Analysis of 2-Aminobenzoic Acid Labeled N-Glycans

The analysis was performed as described in Anumula et al. (1998) Glycobiology, 8:685-694, with minor modifications. N-glycans released from 200 μg of antibody were purified by Biodialyzer overnight. Half of the material was labeled with 2-aminobenzoic acid and cleaned with GlycoClean S cartridge (Prozyme). Several N-glycan standards were also labeled with 2-aminobenzoic acid. 2-aminobenzoic acid labeled glycans were separated on an Asahipak NH2P-50 4D column (4.6×250 mm, Phenomenex) using an HP1100 system equipped with a fluorescence detector (ex. at 230 nm and em. at 425 nm). The column was equilibrated in 70% solvent A (2% acetic acid and 1% inhibited tetrahydrofuran in acetonitrile). 2-aminobenzoic acid labeled glycans were eluted at 50° C. using a linear gradient of 30-50% solvent B (5% acetic acid, 3% triethylamine, and 1% inhibited tetrahydrofuran in water) over 60 minutes at a flow rate of 1 ml/min. Subsequent washes with 95% solvent B and 30% solvent B were used to clean and re-equilibrate the column. Final injection amount equaled to a pool of glycans released from 20 μg of antibody.

Figure 4A:
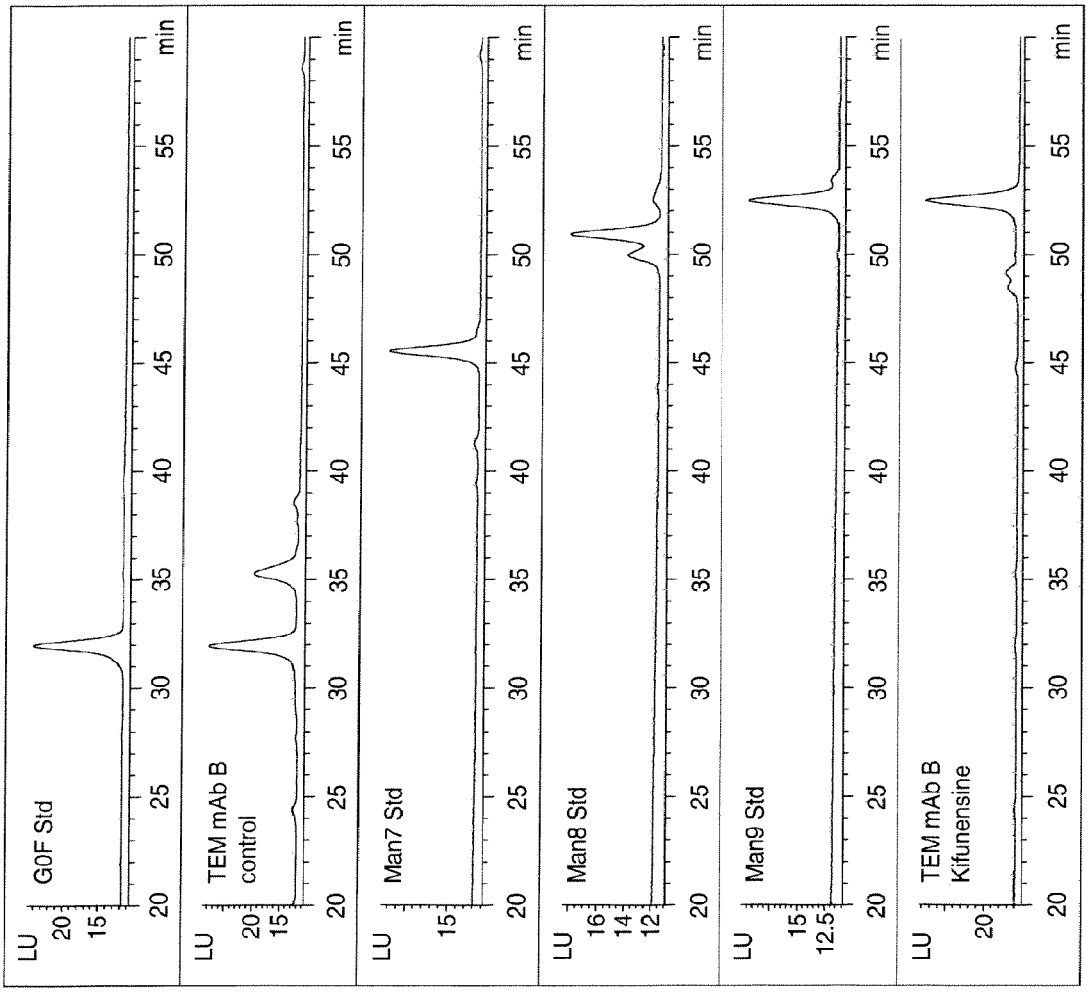
FIG. 4 shows results of an HPLC profiling of 2-aminobenzoic acid labeled N-glycans on TEM mAb B from cells treated with kifunensine or without same. HPLC profiles of 2-aminobenzoic acid labeled N-glycans on TEM mAb B from cells treated with or without kifunensine compared to various N-glycan standards (A). HPLC profiles of 2-aminobenzoic acid labeled N-glycans on TEM mAb B from cells treated with kifunensine before and after Endo H treatment (B).
Figure 4B:
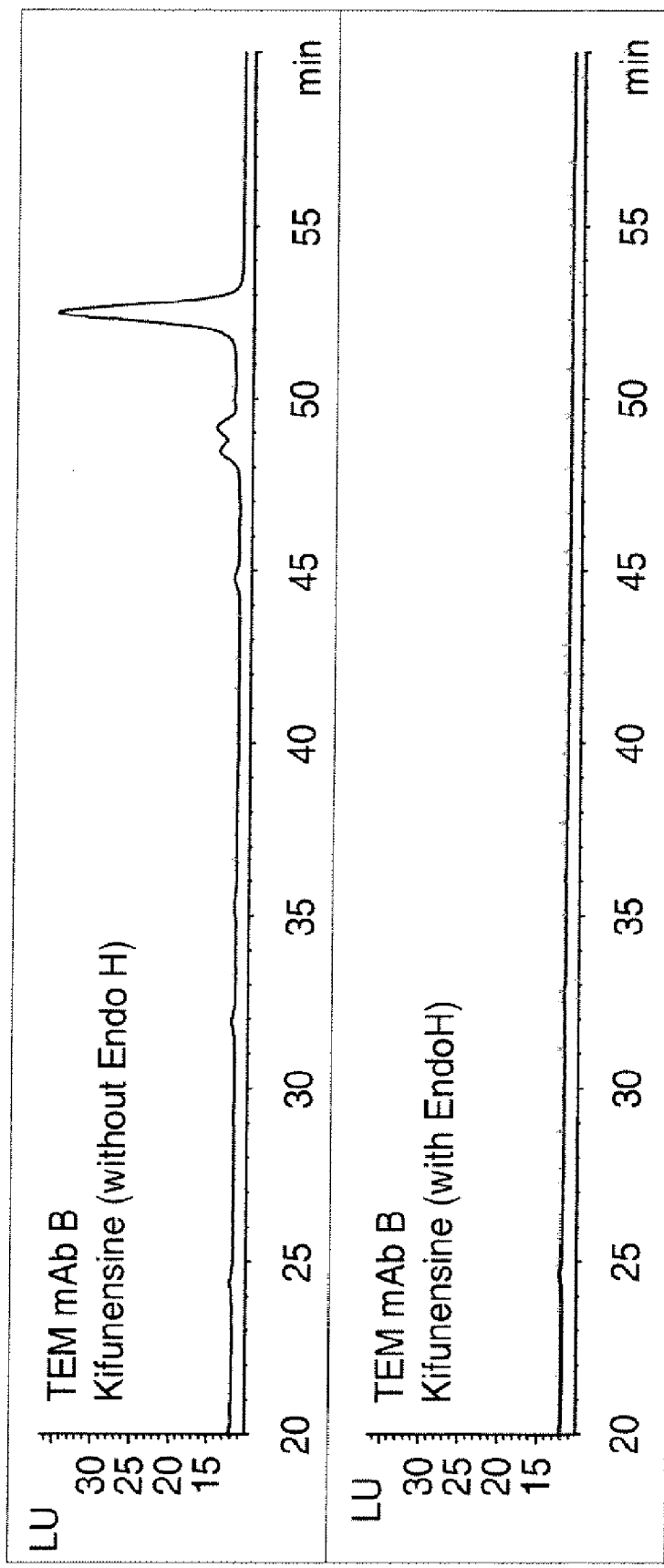

The results of the HPLC analysis of fluorescence labeled N-glycans confirmed the results from MALDI-TOF mass spectrometry analysis (Example 3). For control TEM mAb B, the first peak in HPLC aligned with the G0F standard (FIG. 4A). The other two remaining peaks are presumed to be G1F and G2F. In the spectra of TEM mAb B from cells treated with kifunensine, the last and major MALDI peak aligned with the Man9 standard. However, the presumed Man7 and Man8 peaks from the antibody did not align with the Man7 and Man8 standards. The difference in elution time between the Man7 and Man8 standards and the sample peaks could be attributed to different isomer compositions of those structures. Endo H digestion of fluorescently labeled N-glycans from TEM mAb B from cells treated with kifunensine resulted in the disappearance of the Man9, Man8 and Man7 peaks, confirming their oligomannose structural identity (FIG. 4B).

Example 5

ADCC Assays

The antibody samples from cells treated with different inhibitors were analyzed for ADCC as follows. Target cells, breast cancer cell lines including SKOV3 or MDA231 with TEM antigens, were resuspended in growth media and labeled with Na$_2$$^{51}$CrO$_4$ in a 37° C. incubator with 5% CO$_2$ for 1-2 hrs. The cells were then washed, resuspended in the RPMI medium and mixed with various concentrations of antibodies and effector cells at an effector:target ratio of 100:1 or 200:1. The effector cells were peripheral blood mononuclear cells (PBMC) prepared using Ficoll-Hypaque-gradient centrifugation. The cells and antibodies were incubated for 4-18 hrs at 37° C. in a humidified incubator with 5% CO$_2$. After the incubation, the intact cells were removed by centrifugation or lyzed using detergent. The radioactivity in the supernatants from experimental release (E), spontaneous release (S, release from target without effector cells and antibody), and total lysate (T, release from target cells treated with detergent) was determined using an irradiation counter. The percent specific lysis was calculated as follows: [(E−S)/(T−S)]*100.

Figure 5A:
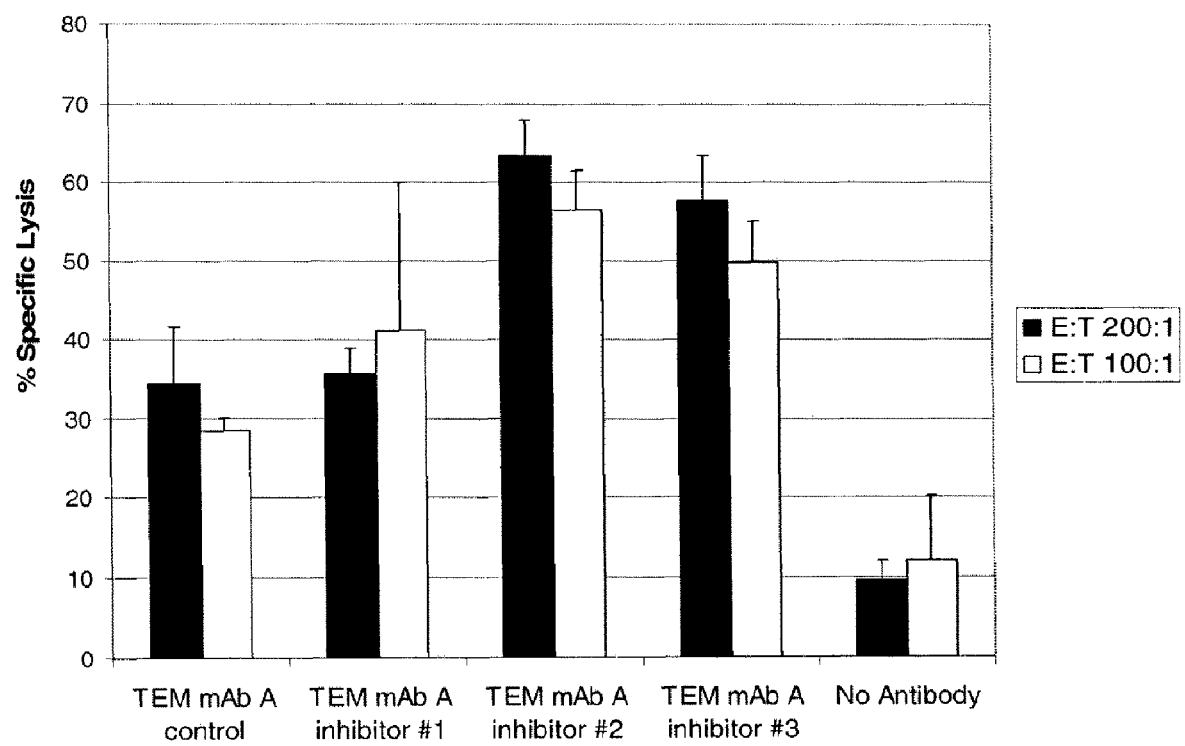
FIG. 5 shows ADCC activity of TEM mAb from cells treated with inhibitors. (A) ADCC activity of TEM mAb A from cells treated without inhibitor (control) or with mannostatin A (inhibitor #1), kifunensine (inhibitor #2), NB-DNJ (inhibitor #3). (B) ADCC activity of TEM mAb A from cells treated without (control) or with kifunensine at various antibody concentrations. (C) ADCC activity of TEM mAb B from cells treated without kifunensine (control) or with kifunensine. Anti-DNP was included in the assays as a negative control.

The results from ADCC assays of TEM mAb A antibodies from hybridoma cells expressed in the presence of various inhibitors are shown in FIG. 5A. The data show that TEM mAb A from hybridoma cells treated with kifunensine (inhibitor #2) had the highest ADCC activity among the antibody samples. The antibody from cells treated with NB-DNJ (inhibitor #3) showed a lower ADCC activity than the same antibody from the kifunensine-treated cells, but a higher activity as compared to all the rest of the samples. The ADCC activity of TEM mAb A from cells treated with mannostatin A (inhibitor #1), was comparable to the control samples. The results indicated that the ADCC activity correlated with the glycosylation patterns of the antibodies.

Figure 5B:
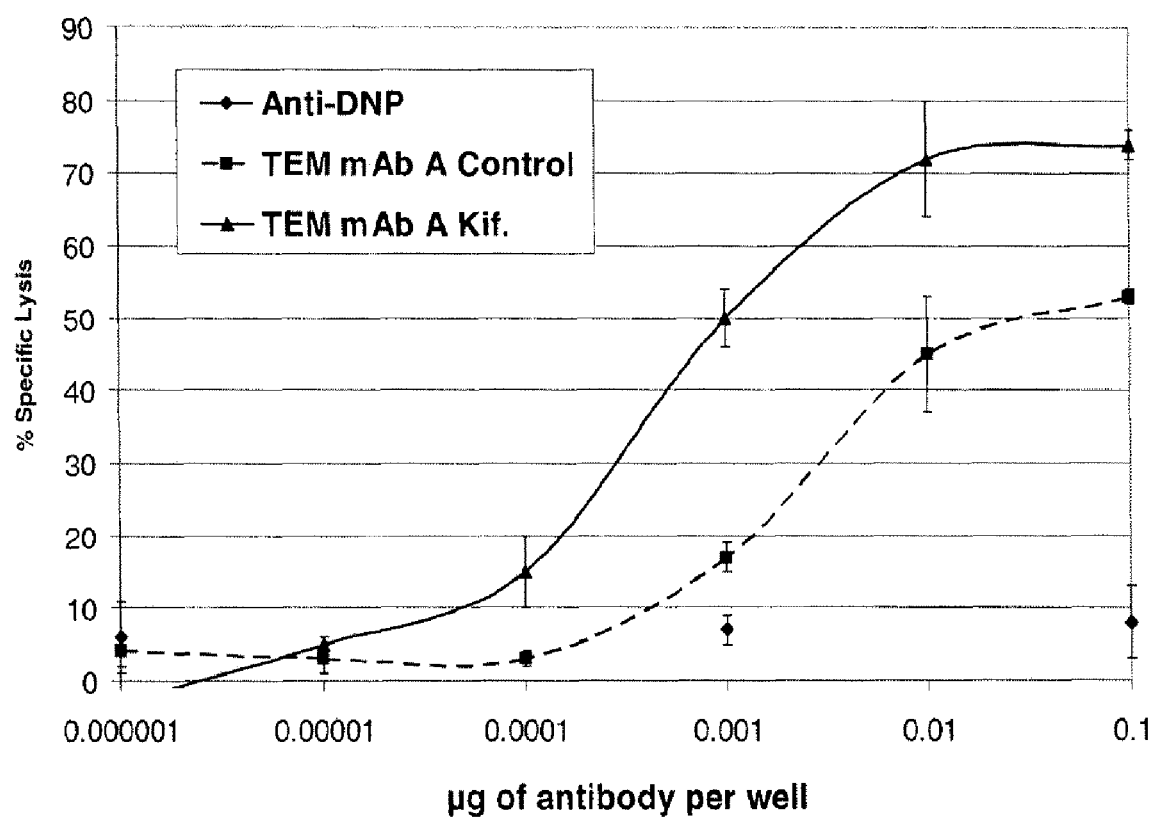
Figure 5C:
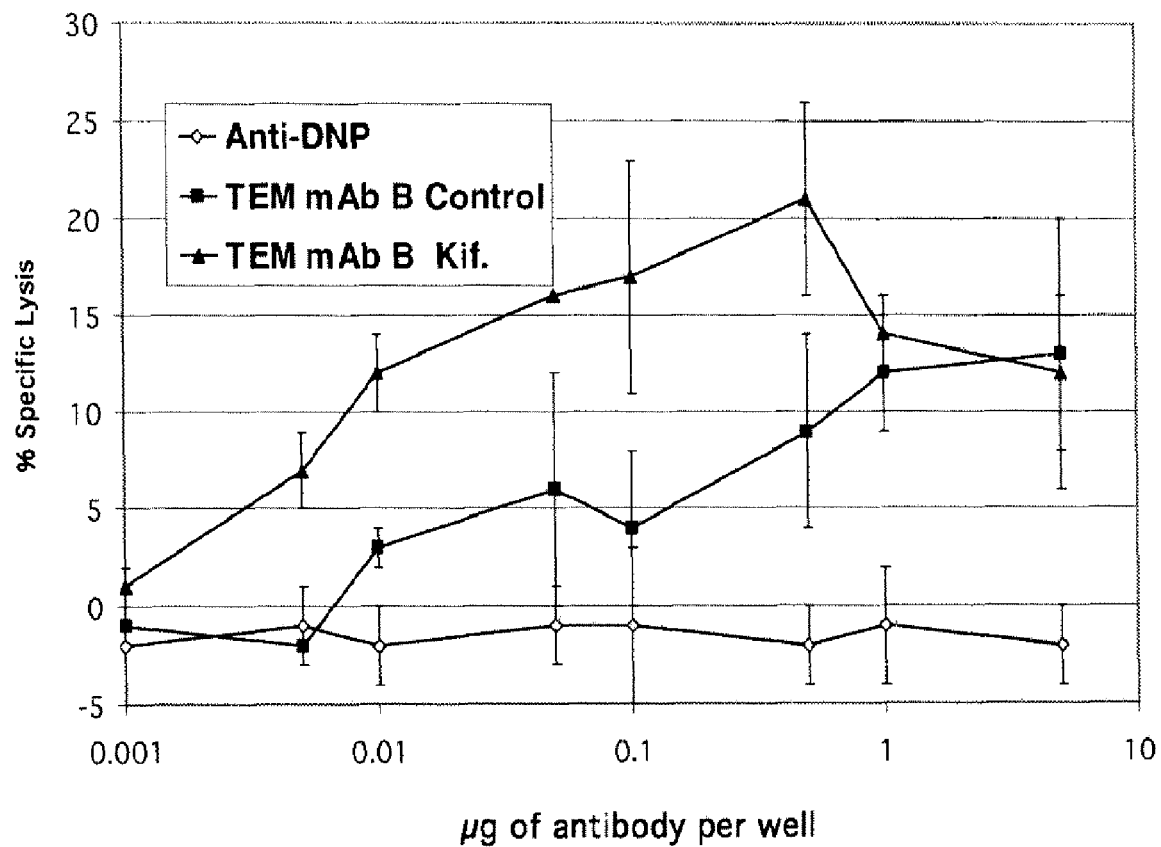

A similar ADCC assay was performed with TEM mAb A produced by kifunensine (inhibitor #2)-treated cell as well as untreated control cells. The results (FIG. 5B) showed a 10-100-fold increase in ADCC activity for the antibody from cells treated with kifunensine as compared to that from hybridoma cells treated without inhibitor (control). Another similar ADCC assay was also performed on TEM mAb B from CHO cells treated with kifunensine and untreated controls. The results (FIG. 5C) showed that TEM mAb B from kifunensine-treated cells produced antibody with a higher ADCC activity than the controls.

Example 6

Flow Cytometry Analysis

A FACS® assay was performed to determine the binding of TEM mAb A and TEM mAb B to antigens on target cells. 2×105 target cells were incubated with antibody from cells treated with various inhibitors as described in Example 5. The incubating solution contained 1 to 10 µg/ml antibody in PBS with 5% fetal bovine serum and 5% goat serum. The bound antibody was detected with FITC-labeled goat anti-human Fc and analyzed using a FACS Calibur (Becton Dickinson).

Figure 6A:
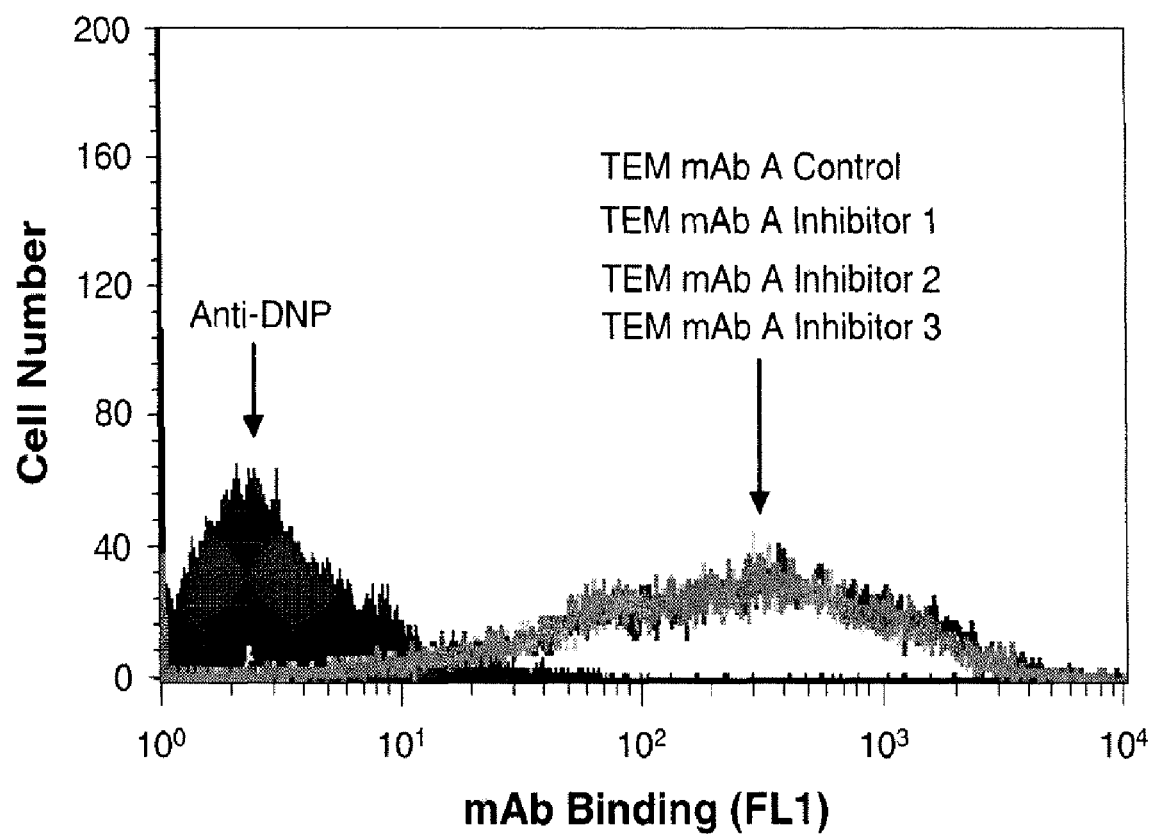
FIG. 6A shows TEM mAb A binding to target cells by flow cytometric analysis. The antibody from cells treated without inhibitor is labeled as control, while the antibody from cells treated with mannostatin A (inhibitor #1), kifunensine (inhibitor #2), and NB-DNJ (inhibitor #3) are labeled as such.
Figure 6B:
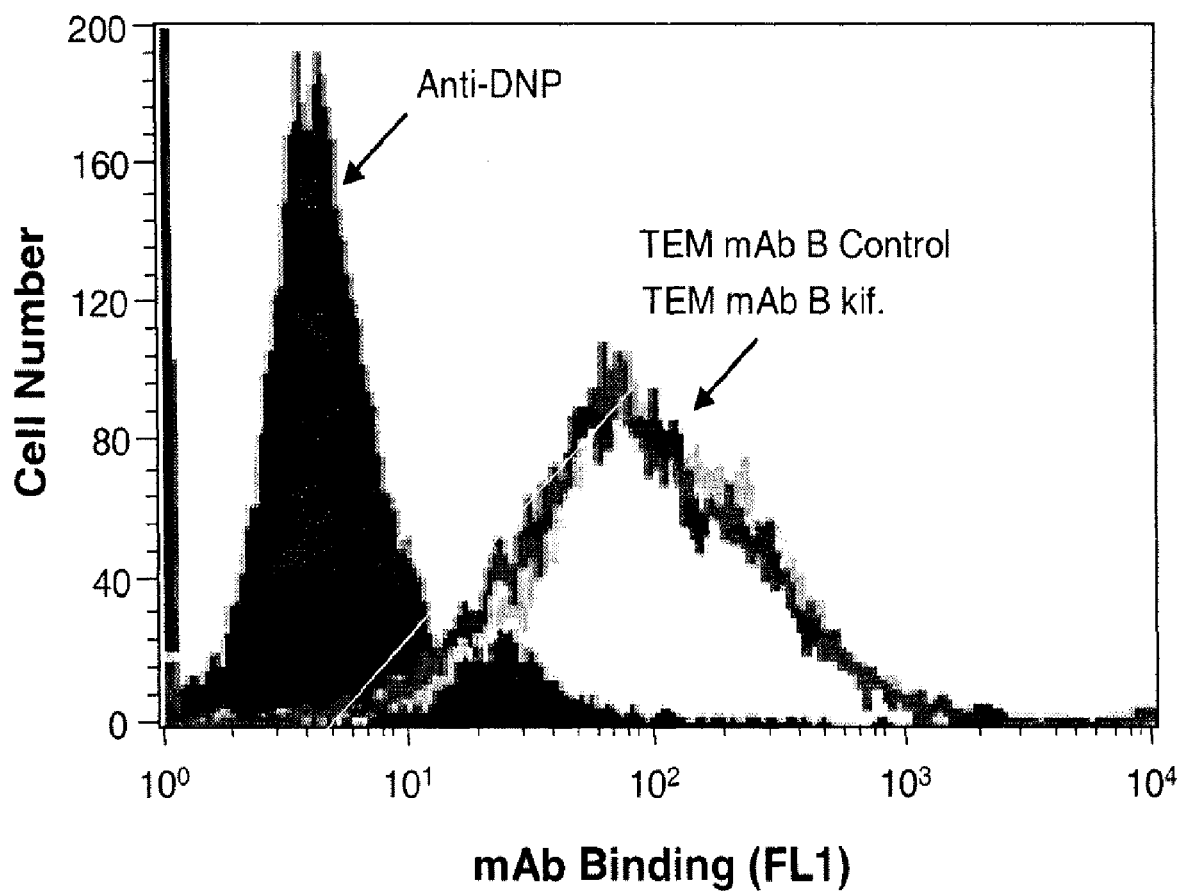
FIG. 6B shows TEM mAb B binding to target cells by flow cytometric analysis. The TEM antibodies were from cells treated without (control) or with kifunensine, while anti-DNP was also included as a negative control.

The results of the FACS® analysis indicate that despite the difference in the ADCC activities (see Example 5), TEM mAb A (FIG. 6A) and TEM mAb B (FIG. 6B) bound equally well to the cell surface antigens regardless of whether they were produced with or without kifunensine.

Example 7

Fc Receptor and Mannose Receptor Binding

Since ADCC activity is correlated with the binding of the antibody or antibody-antigen complex to Fc receptors, especially FcγRIIIA, the interaction of antibodies with FcγRIIIA was investigated using surface plasmon resonance. TEM mAb B was immobilized on CM5 chip with a TEM antigen. Soluble recombinant human FcγRIIIA (Val158) was then injected into BIAcore™ 3000 biosensor unit to monitor the binding.

Figure 7:
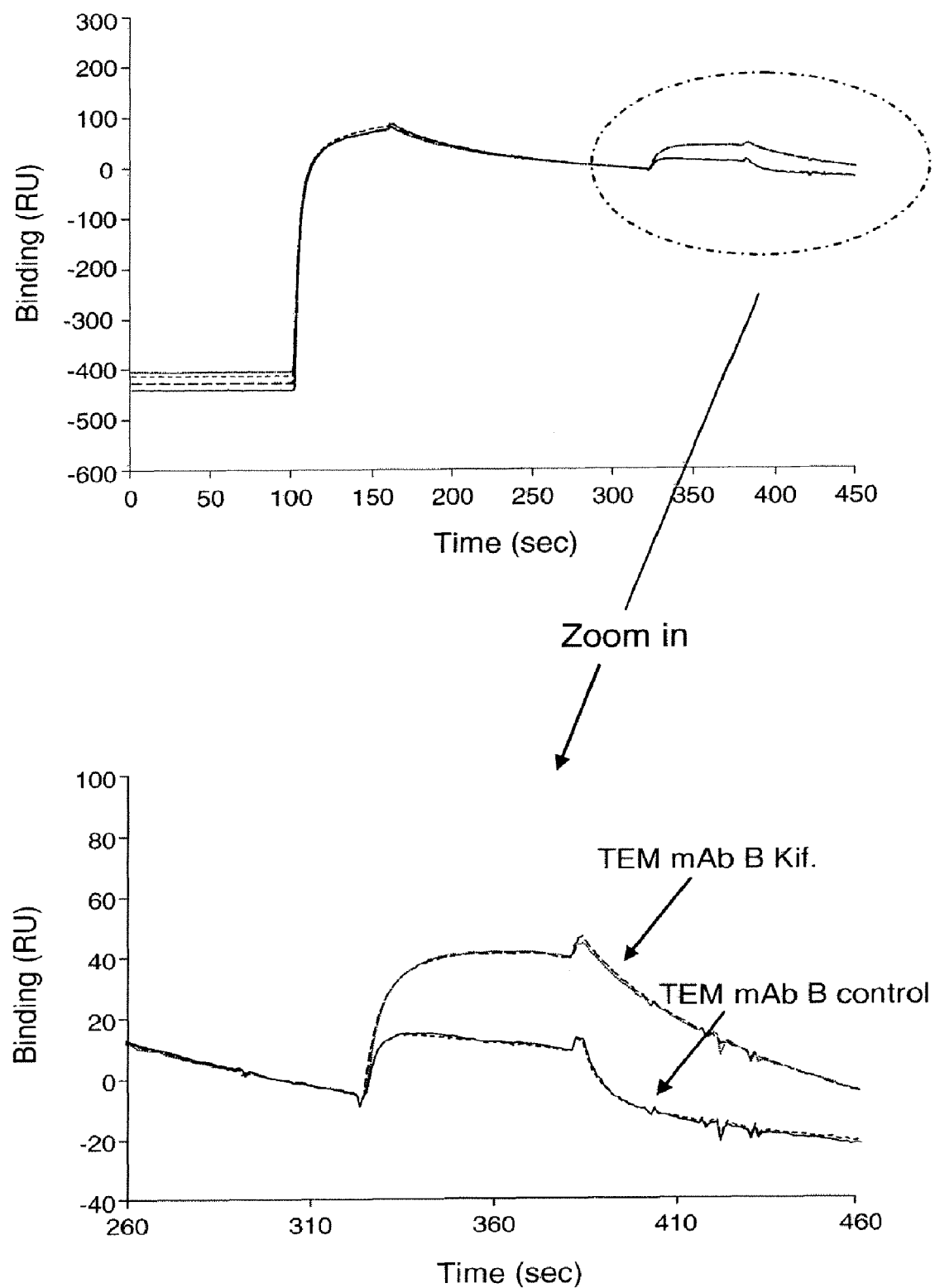
FIG. 7 shows results of a surface plasmon resonance analysis of the interaction between soluble human FcγRIIIA (Val158) and antibodies produced from cells treated with kifunensine and untreated cells. The region of interest was expanded to show the flow of FcγRIIIA.

The results (FIG. 7) indicated a higher FcγRIIIA binding to TEM mAb B expressed in the presence of kifunensine as compared to the same antibody expressed in the absence of the inhibitor. The increased binding of antibody from kifunensine-treated cells to the Fc receptor correlated with the enhancement of ADCC activity of these antibodies.

The in vivo clearance through the mannose receptor is known to be quite rapid. Accordingly, the binding of the TEM mAb B to the mannose receptor was investigated using surface plasmon resonance (BIAcore™). A soluble mannose receptor containing carbohydrate recognition domain (CRD) 4-7 and a HPC tag was immobilized to a CM5 BIAcore surface (200 RU). The antibodies were diluted to 100 nM in HBS binding buffer (10 mM HEPES, pH 7.0, 150 mM NaCl) containing 10 mM $CaCl_2$ and 0.005% surfactant P20 and injected into a BIAcore™ 3000 biosensor unit to monitor the binding. Mannose terminated glucocerebrosidase (100 nM) was included as a positive control.

Figure 8:
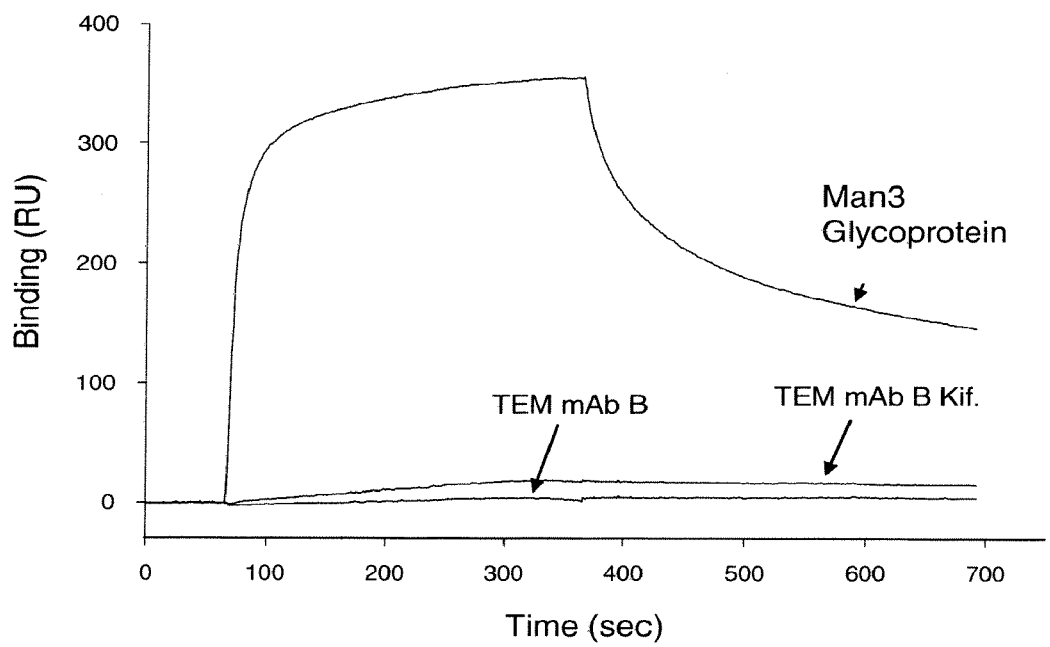
FIG. 8 demonstrates the interaction of the carbohydrate-binding domain of the mannose receptor with antibodies from cells treated with or without kifunensine. Binding of TEM mAb B from CHO cells treated with or without kifunensine to the carbohydrate-binding domain of the mannose receptor was measured using BIAcore™. Mannose terminated glycoprotein ("Man3 glycoprotein") was used as a positive control.

The results of the mannose receptor binding experiments (FIG. 8) showed that the binding of the antibody from either kufinensine-treated or kifunensine untreated cells was much lower than the control (protein with oligomannose type N-glycans such as $Man_3(GlcNAc)_2$ ("Man3 glycoprotein"). These results suggest that, when administered in vivo, the antibodies carrying oligomannose type glycans are not likely to be rapidly cleared by the mannose receptor.

Example 8

Antibody Affinity Analysis

The binding affinity of TEM mAb B expressed in the presence of kifunensine was compared to the antibody expressed in the absence of the inhibitor using surface plasmon resonance (BIAcore™) as follows. The affinity of antibody was measured using CM5 chips carrying immobilized antigen. Antibodies diluted in different concentrations using HBS-EP or PBS containing 0.005% surfactant P20 running buffer were injected in duplicate or triplicate for 5 min, followed by 5 min dissociation. 40 mM HCl was used to regenerate the surface. A 1:1 binding model was then used to fit the data.

The results (Table 2) showed comparable affinities of TEM mAb B expressed in the presence or in the absence of kifunensine, when a 1:1 binding model was used to fit the data. The sensorgrams showed nearly identical binding curves for both of the samples at each concentration tested. These results were consistent with the data on the antibody binding to the antigen on target cells using FACS (Example 6).

TABLE 2

| TEM-1 mAb B (CHO) | $k_a^a$ (1/Ms × $10^6$) | $k_d^b$ (1/s × $10^{-3}$) | $K_A^c$ (1/M × $10^9$) | $K_D^d$ (M × $10^{-9}$) |
|---|---|---|---|---|
| untreated | 1.16 | 1.14 | 1.01 | 0.99 |
| kifunensine treated | 1.44 | 1.18 | 1.22 | 0.82 |

$^a$on rate;
$^b$off rate;
$^c$association rate;
$^d$dissociation rate.

Example 9

Pharmacokinetic Analysis

A pharmacokinetic analysis was performed using mice injected with TEM mAb B expressed in the presence or absence of kifunensine. TEM mAb B injected into BALB/c mice via tail vein at 5 mg/kg. There were ten mice per group. The blood was collected at 1, 6 hours and 1, 2, and 7 days after injection and kept frozen. The amount of TEM mAb B in the serum was measured using ELISA with anti-human antibodies.

Figure 9:
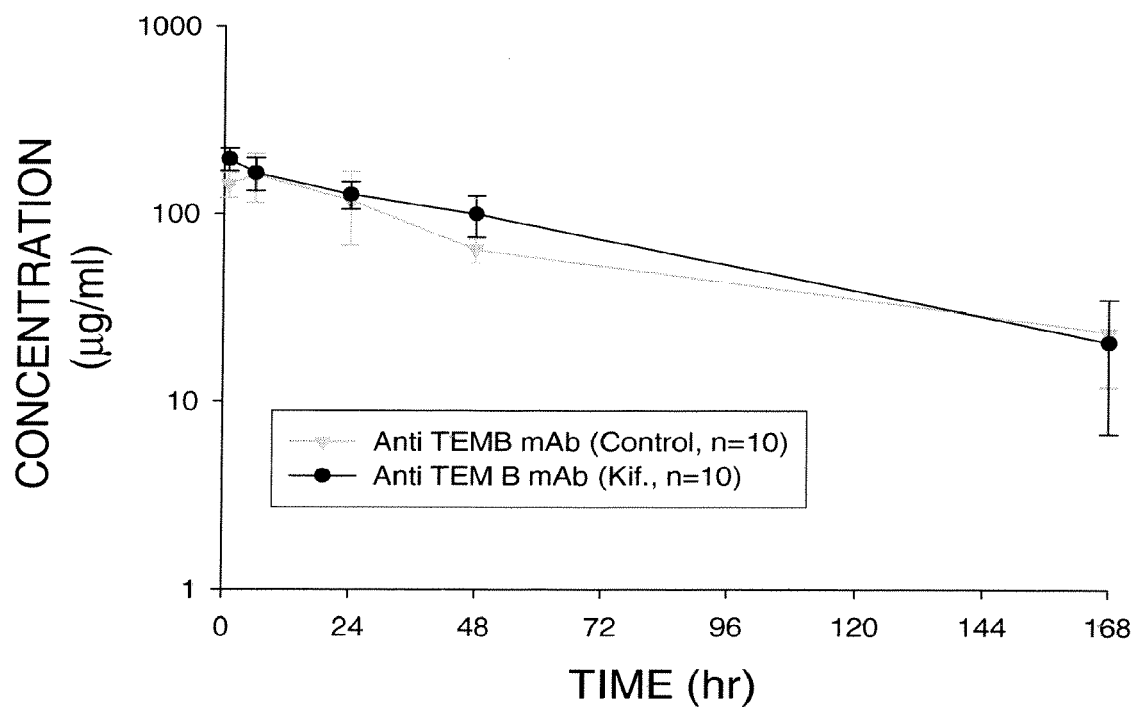
FIG. 9 shows results of a pharmacokinetic analysis of TEM mAb B from CHO cells treated with or without kifunensine. TEM mAb B from CHO cells treated with or without kifunensine was injected into mice and the amount of antibodies in sera collected at various time points was measured using ELISA.

The results are presented in FIG. 9. There was no significant difference in the apparent elimination half-life of TEM mAb B samples from cells treated with or without kifunensine. Little difference in the amount of both antibodies was observed in the sera of mice on day 7 post-injection. The results suggest that oligomannose-type glycans on TEM mAb did not contribute to significant clearance via the mannose receptor based on the in vitro mannose receptor binding data (Example 7) and the pharmacokinetics.

Example 10

Production of Antibody in Batch Cultures

The production of TEM mAb B from batch cultures treated with various amounts of kifunensine or untreated was evaluated. CHO cells in shaker flasks were treated with 0, 0.5, 1, 1.5, or 2 µg/ml in a single or three additions (4 days apart) and cultured for 11 days. Cell viability (using trypan blue) and cell counts were assessed at least every other day.

Figure 10A:
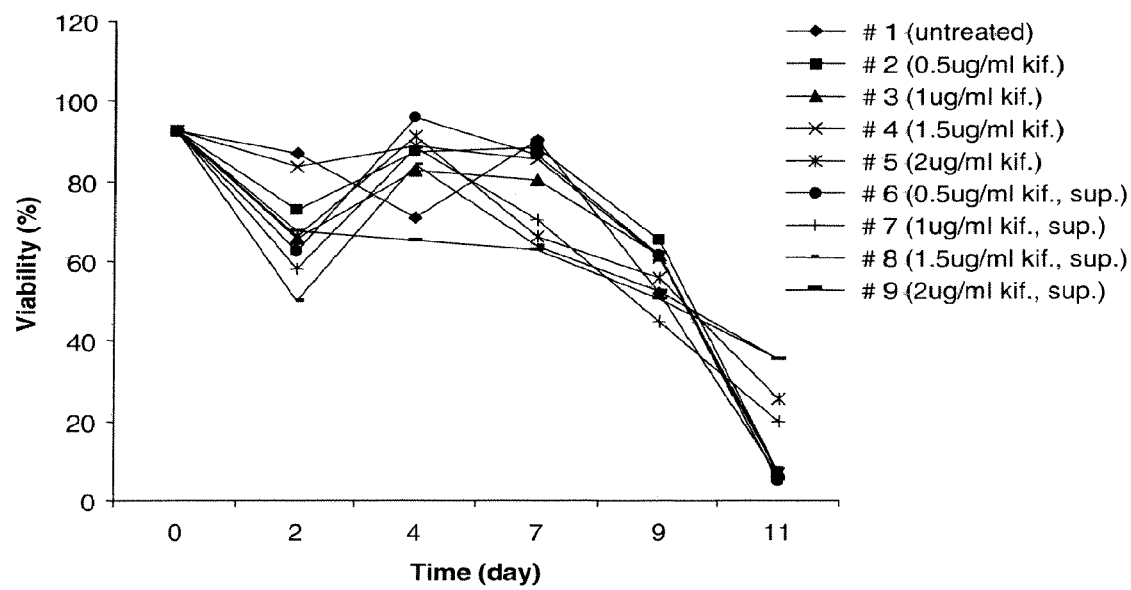
FIG. 10A illustrates viability of CHO cells expressing TEM mAb B grown in shaker flasks in media with 0 to 2 µg/ml kifunensine (1 or 3 treatments).
Figure 10B:
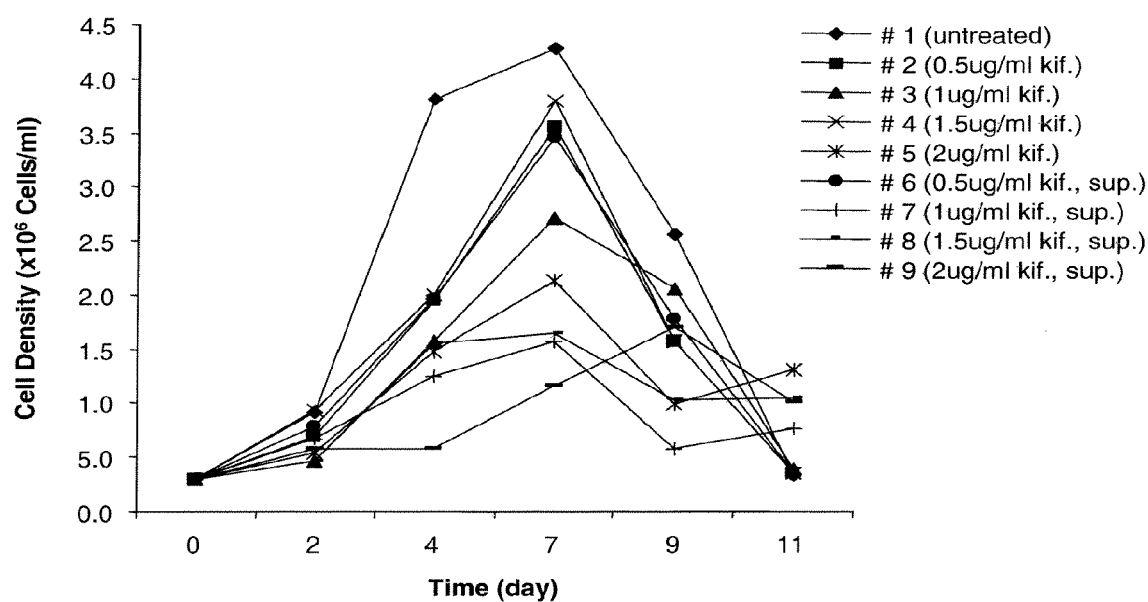
FIG. 10B illustrates cell density of CHO cells expressing TEM mAb B grown in media with or without 0 to 2 µg/ml kifunensine (1 or 3 treatments). The 3x treatment is indicated as "sup.

The antibody VPR (volume production rate) during the 11 days in culture with a single kifunensine treatment at concentrations from 0.5 to 2 µg/ml was comparable to that in the triple treatments at the same amounts of the inhibitor. The results showed similar amount of antibody produced under different conditions (Table 3). The cell viability was comparable for different conditions (FIG. 10A), while the cell density was lower in kifunensine-treated cells. The treatment of cells with three additions of kifunensine resulted in a much lower cell density than that in the untreated control or the single kifunensine treatment (FIG. 10B and Table 3).

The effect of kifunensine on the production of TEM mAb A in batch cultures was likewise tested. Cells were cultured in 1 L spinners for 11 days in the media with 2 µg/ml kifunensine (single addition) or without. Cell viability (using trypan blue) and cell counts were assessed at least every other day.

TABLE 3

| Sample | VPR (mg/l)$^a$ | Xvmax$^b$ (×10$^6$ cells) | SPR (average)$^c$ Pg/cell/day |
|---|---|---|---|
| #1, untreated | 350.6 | 4.3 | 14.9 |
| #2, 0.5 µg/ml kif | 390.1 | 3.5 | 20.0 |
| #3, 1 µg/ml kif | 386.9 | 2.7 | 26.0 |
| #4, 1.5 µg/ml kif | 387.6 | 3.8 | 18.6 |
| #5, 2 µg/ml kif | 371.8 | 2.1 | 31.7 |
| #6, 0.5 µg/ml kif sup. 3x | 397.7 | 3.5 | 21.0 |
| #7, 1 µg/ml kif sup. 3x | 376.1 | 1.6 | 43.6 |
| #8, 1.5 µg/ml kif sup. 3x | 377.7 | 1.6 | 41.9 |
| #9, 2 µg/ml kif sup. 3x | 341.0 | 1.7 | 36.5 |

$^a$volume production rate;
$^b$viable cells at day of peak cell density;
$^c$specific production rate.

Figure 11A:
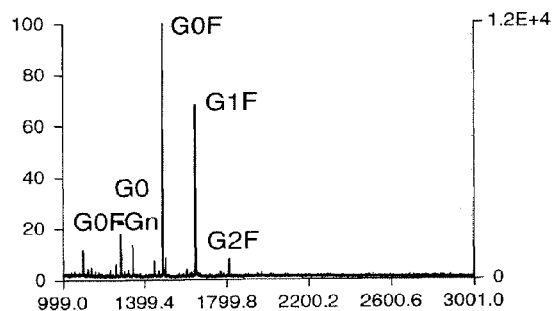
FIG. 11 shows results of a matrix-assisted laser desorption/ionization time-of-flight (MALDI-TOF) mass spectrometry analysis of carbohydrates from TEM antibodies from CHO cells treated with various amounts of kifunensine for 11 days. Carbohydrates on TEM mAb B from cells treated without kifunensine (FIG. 11A) or with the following additions of kifunensine are as follows.
(FIG. 11B) 0.5 µg/ml once, (FIG. 11C) 1 µg/ml once, (FIG. 11D) 1.5 µg/ml once, (FIG. 11E) 2 µg/ml once, (FIG. 11F) 0.5 µg/ml thrice, (FIG. 11G) 1 µg/ml thrice, (FIG. 11H) 1.5 µg/ml thrice, and (FIG. 11I) 2 µg/ml thrice (see FIG. 10). Carbohydrates on TEM mAb A from cells treated without inhibitor (FIG. 11J) or 2 µg/ml kifunensine for 11 days (FIG. 11K) (see also FIG. 12).
Figure 11B:
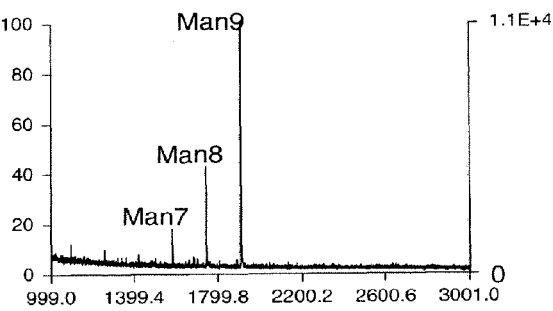
Figure 11C:
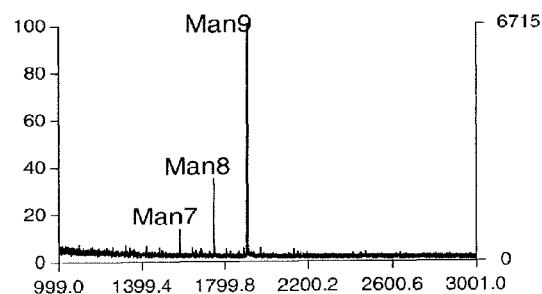
Figure 11D:
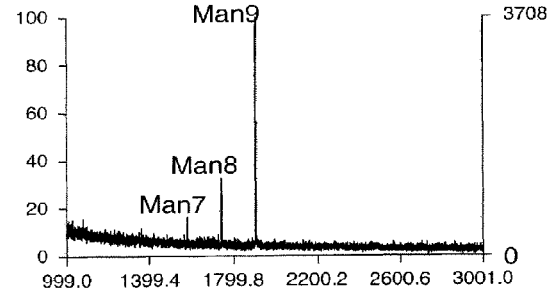
Figure 11E:
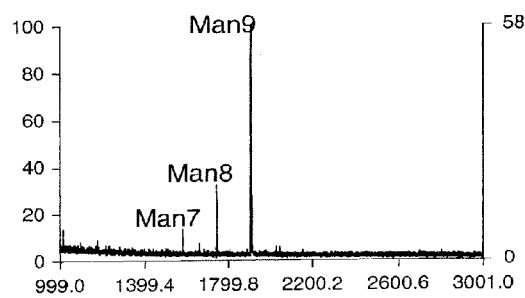
Figure 11F:
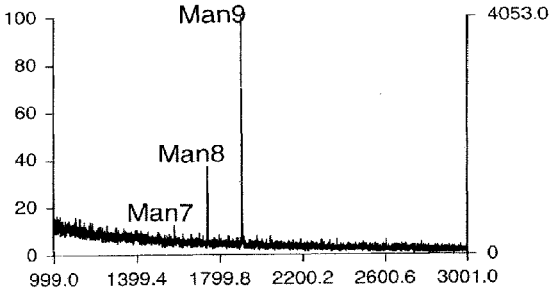
Figure 11G:
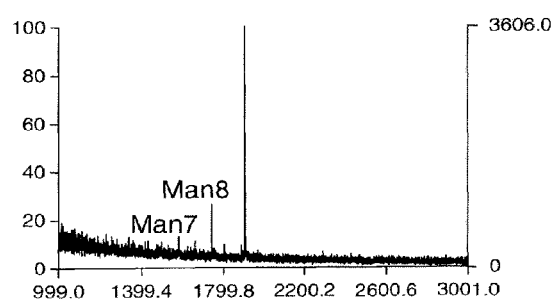
Figure 11H:
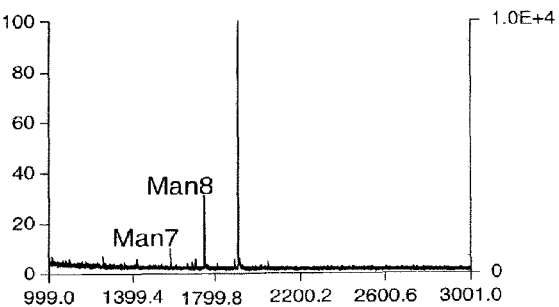
Figure 11I:
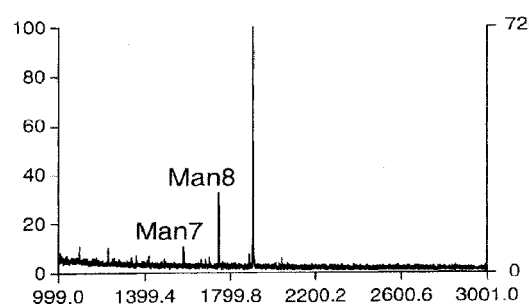
Figure 11J:
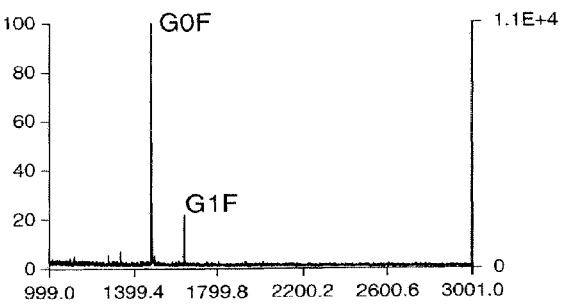
Figure 11K:
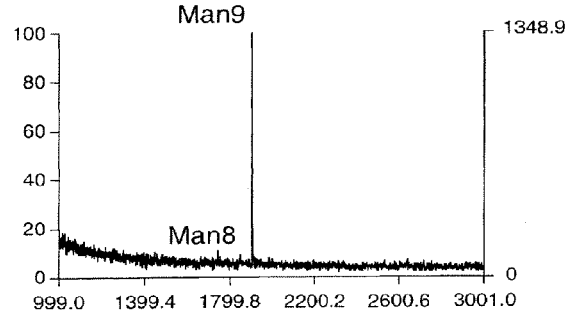
Figure 12A:
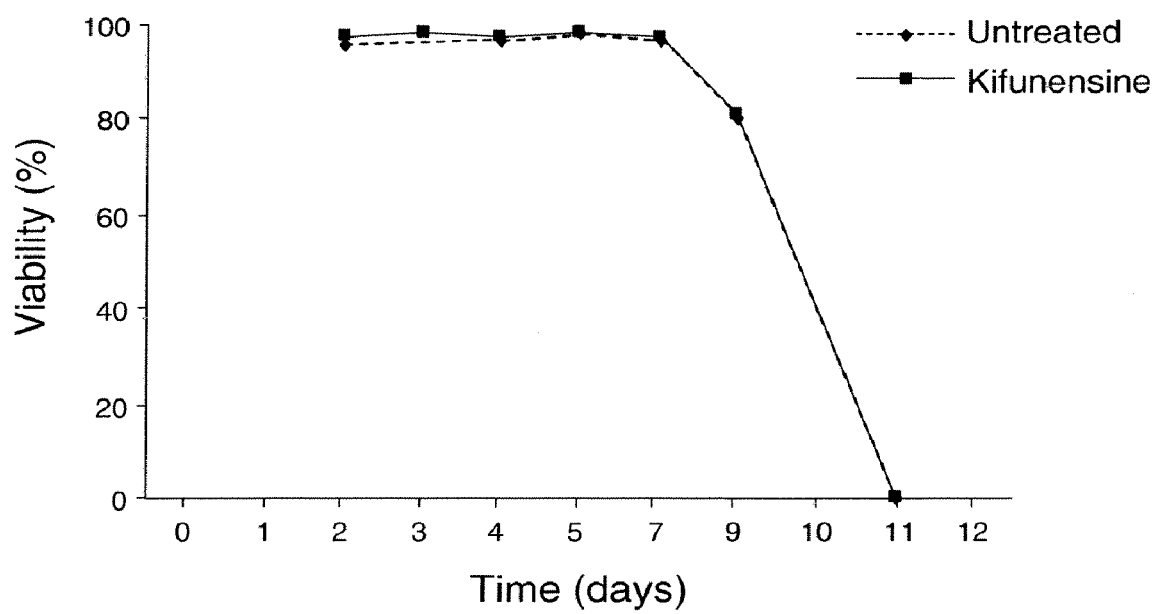
FIG. 12A illustrates viability of CHO cells expressing TEM mAb A grown in media with or without 2 µg/ml kifunensine for 11 days (single treatment in 1 L spinner culture).
Figure 12B:
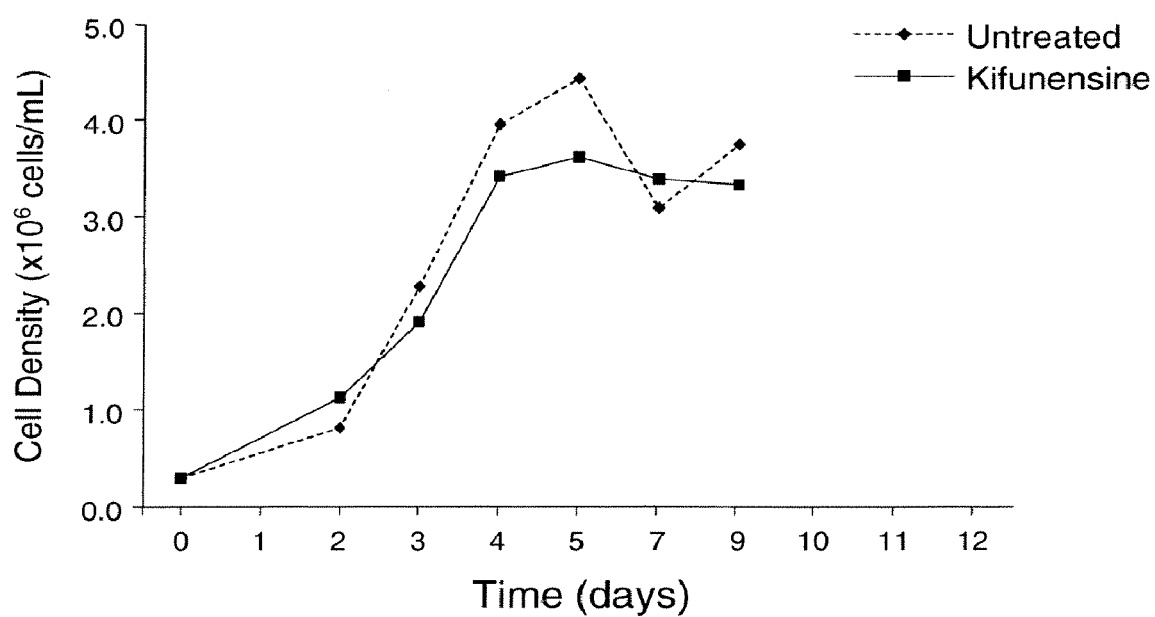
FIG. 12B illustrates cell density of CHO cells expressing TEM mAb A grown in media with or without 2 µg/ml kifunensine (single addition).

The results showed similar cell viability and cell counts (FIG. 12). About 60% increase in the antibody titer was observed with kifunensine as compared to controls. The results from MALDI-TOF mass spectrum analysis also indicated the presence of Man8- and Man9-containing N-glycans as major species in TEM mAb A from cells treated with kifunensine (FIG. 11K). The carbohydrates in TEM mAb B purified from these cultures contained similar Man9- and Man8-containing N-glycans regardless of the amount of kifunensine used (FIG. 11 and Table 4). A single kifunensine treatment at a concentration of 0.5 µg/ml was enough to result in the production of oligomannose-type structures.

Kifunensine treatment did not affect the cell viability or antibody production. Cell growth was retarded, especially in the high dose and multiple kifunensine treatments, in CHO cells in shaker flask but not so in the spinner cultures, suggesting that the kifunensine treatment may have resulted in an increased antibody expression and/or secretion efficiency.

TABLE 4

| Groups | Observed$^a$ m/z | Theoretical$^a$ m/z | Structures |
|---|---|---|---|
| #1, untreated | 1486.1199 (peak 1) | 1485.5344 | (HexNAc)$_2$(Deoxyhexose)$_1$ + (Man)$_3$(GlcNAc)$_2$ G0F |
| | 1648.2581 (peak 2) | 1647.5874 | (Hex)$_1$(HexNAc)$_2$(Deoxyhexose)$_1$ + (Man)$_3$(GlcNAc)$_2$ G1F |
| | 1282.9616 (peak 3) | 1282.4553 | (HexNAc)$_1$(Deoxyhexose)$_1$ + (Man)$_3$(GlcNAc)$_2$ G0F-Gn |
| | 1340.0094 (peak 4) | 1339.4763 | (HexNAc)$_2$ + (Man)$_3$(GlcNAc)$_2$ G0 |
| | 1810.3561 (peak 5) | 1809.6403 | (Hex)$_2$(HexNAc)$_2$(Deoxyhexose)$_1$ + (Man)$_3$(GlcNAc)$_2$ G2F |
| #2, 0.5 µg/ml kif | 1906.6223 (peak 1) | 1905.6343 | (Hex)$_6$ + (Man)$_3$(GlcNAc)$_2$ Man9 without fucose |
| | 1744.4747 (peak 2) | 1743.5813 | (Hex)$_5$ + (Man)$_3$(GlcNAc)$_2$ Man8 without fucose |
| | 1582.3702 (peak 3) | 1581.5283 | (Hex)$_4$ + (Man)$_3$(GlcNAc)$_2$ Man7 without fucose |
| #3, 1 µg/ml kif | 1906.4626 (peak 1) | 1905.6343 | (Hex)$_6$ + (Man)$_3$(GlcNAc)$_2$ Man9 without fucose |
| | 1744.3398 (peak 2) | 1743.5813 | (Hex)$_5$ + (Man)$_3$(GlcNAc)$_2$ Man8 without fucose |
| | 1582.2029 (peak 3) | 1581.5283 | (Hex)$_4$ + (Man)$_3$(GlcNAc)$_2$ Man7 without fucose |
| #4, 1.5 µg/ml kif | 1906.7339 (peak 1) | 1905.6343 | (Hex)$_6$ + (Man)$_3$(GlcNAc)$_2$ Man9 without fucose |
| | 1744.5612 (peak 2) | 1743.5813 | (Hex)$_5$ + (Man)$_3$(GlcNAc)$_2$ Man8 without fucose |
| | 1582.4397 (peak 3) | 1581.5283 | (Hex)$_4$ + (Man)$_3$(GlcNAc)$_2$ Man7 without fucose |

TABLE 4-continued

| Groups | Observed[a] m/z | Theoretical[a] m/z | Structures |
|---|---|---|---|
| #5, 2 μg/ml kif | 1906.7511 (peak 1) | 1905.6343 | $(Hex)_6 + (Man)_3(GlcNAc)_2$ Man9 without fucose |
| | 1744.5969 (peak 2) | 1743.5813 | $(Hex)_5 + (Man)_3(GlcNAc)_2$ Man8 without fucose |
| | 1582.4309 (peak 3) | 1581.5283 | $(Hex)_4 + (Man)_3(GlcNAc)_2$ Man7 without fucose |
| #6, 0.5 μg/ml kif sup. 3x | 1906.8270 (peak 1) | 1905.6343 | $(Hex)_6 + (Man)_3(GlcNAc)_2$ Man9 without fucose |
| | 1744.6267 (peak 2) | 1743.5813 | $(Hex)_5 + (Man)_3(GlcNAc)_2$ Man8 without fucose |
| | 1582.5494 (peak 3) | 1581.5283 | $(Hex)_4 + (Man)_3(GlcNAc)_2$ Man7 without fucose |
| #7, 1 μg/ml kif sup. 3x | 1906.6577 (peak 1) | 1905.6343 | $(Hex)_6 + (Man)_3(GlcNAc)_2$ Man9 without fucose |
| | 1744.5094 (peak 2) | 1743.5813 | $(Hex)_5 + (Man)_3(GlcNAc)_2$ Man8 without fucose |
| | 1582.4178 (peak 3) | 1581.5283 | $(Hex)_4 + (Man)_3(GlcNAc)_2$ Man7 without fucose |
| #8, 1.5 μg/ml kif sup. 3x | 1906.5720 (peak 1) | 1905.6343 | $(Hex)_6 + (Man)_3(GlcNAc)_2$ Man9 without fucose |
| | 1744.4355 (peak 2) | 1743.5813 | $(Hex)_5 + (Man)_3(GlcNAc)_2$ Man8 without fucose |
| | 1582.3379 (peak 3) | 1581.5283 | $(Hex)_4 + (Man)_3(GlcNAc)_2$ Man7 without fucose |
| #9, 2 μg/ml kif sup. 3x | 1905.8527 (peak 1) | 1905.6343 | $(Hex)_6 + (Man)_3(GlcNAc)_2$ Man9 without fucose |
| | 1743.7679 (peak 2) | 1743.5813 | $(Hex)_5 + (Man)_3(GlcNAc)_2$ Man8 without fucose |
| | 1581.7125 (peak 3) | 1581.5283 | $(Hex)_4 + (Man)_3(GlcNAc)_2$ Man7 without fucose |

[a] m/z values are for the [M + Na]+ ions

Example 11

Additional Example of Enhanced ADCC Activity and Higher FcγRIIIA Binding for an Antibody Produced in Cells Treated with Kifunensine An antibody against a small cell lung carcinoma antigen (antibody C) was produced in cells treated with or without kifunensine. The cDNA for the antibody was transiently transfected into HEK293 cells. On day 2, the medium was removed and fresh medium with 2 μg/ml kifunensine or without kifunensine was added into T-150 3-layer flasks. Medium was harvested after treatment of cells with kifunensine for 3 days. The antibody was purified from 150~200 ml of medium. Purity of antibodies was analyzed using a 4-20% gradient SDS-PAGE, while glycosylation was investigated using a lectin blot. Results from SDS-PAGE analysis indicated a high purity of antibody samples. Much less α-1,6-linked fucose was present in the antibodies expressed in the presence of kifunensine. MALDI-TOF MS analysis showed complete modification of glycans into Man9 and Man8 without fucose in the antibody C expressed in the presence of kifunensine.

Figure 13A:
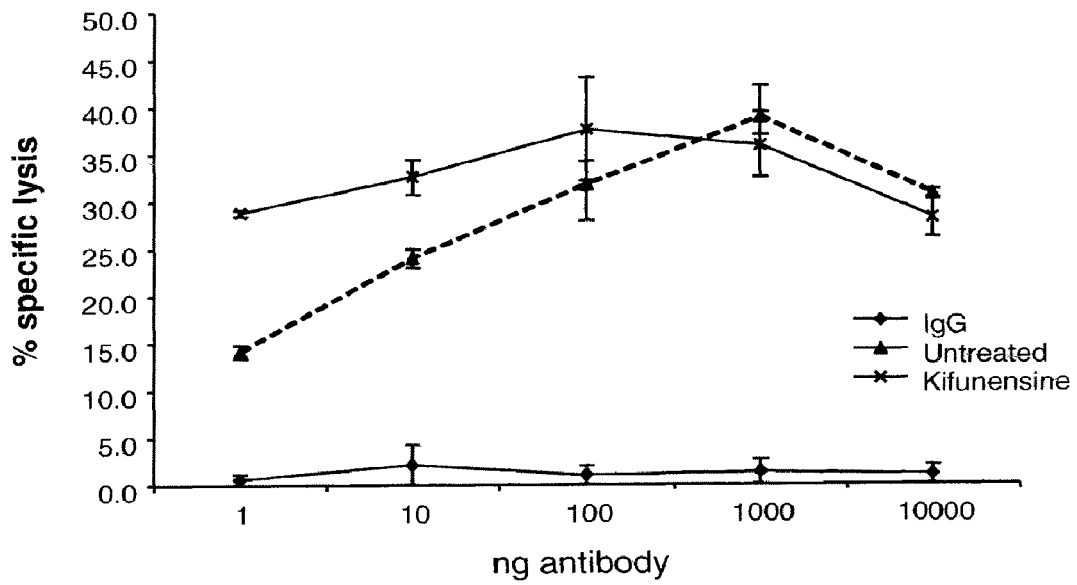
FIG. 13 shows ADCC activity of antibody C expressed by HEK293 cells treated with or without kifunensine. Human PBMC were used as effector cells, and cells which express the antigen recognized by antibody C were used as target cells at 50:1 (FIG. 13A) and 100:1 (FIG. 13B) effector cell to target cell ratio. IgG was used as a non-specific antibody control.
Figure 13B:
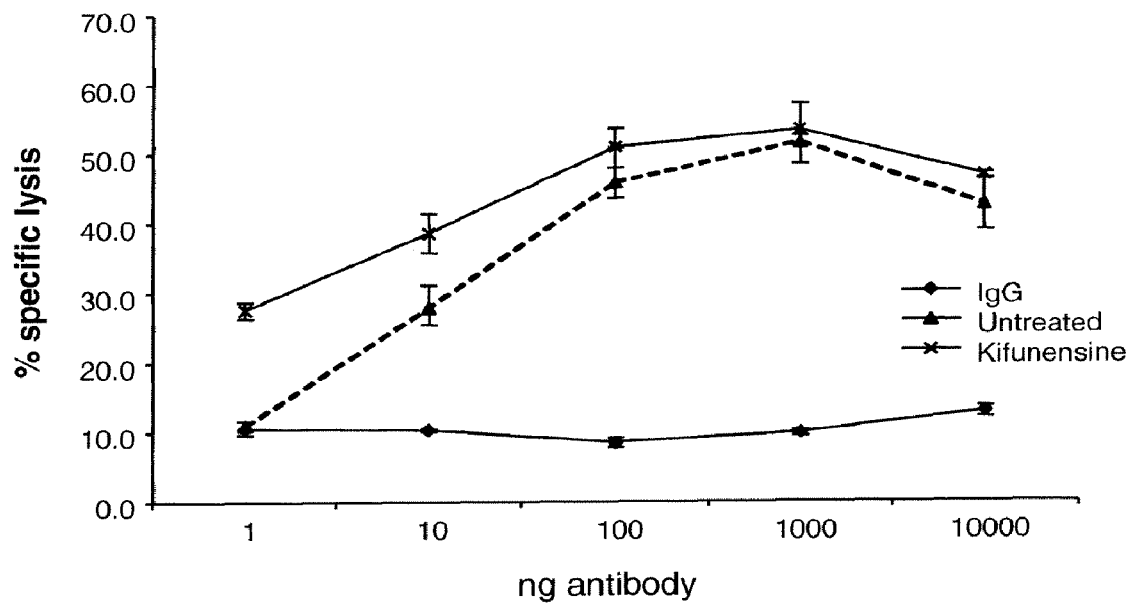

ADCC activity of the two samples was measured using cells endogenously expressing the tumor antigen as target cells. The assay was performed by incubating effector cells (human PBMC) and target cells for 5 hrs at 50:1 or 100:1 ratio. The results, which are shown in FIGS. 13A and 13B, respectively, indicate significant enhancement of ADCC activity of antibody C expressed in the presence of kifunensine at low antibody concentrations.

Figure 14:
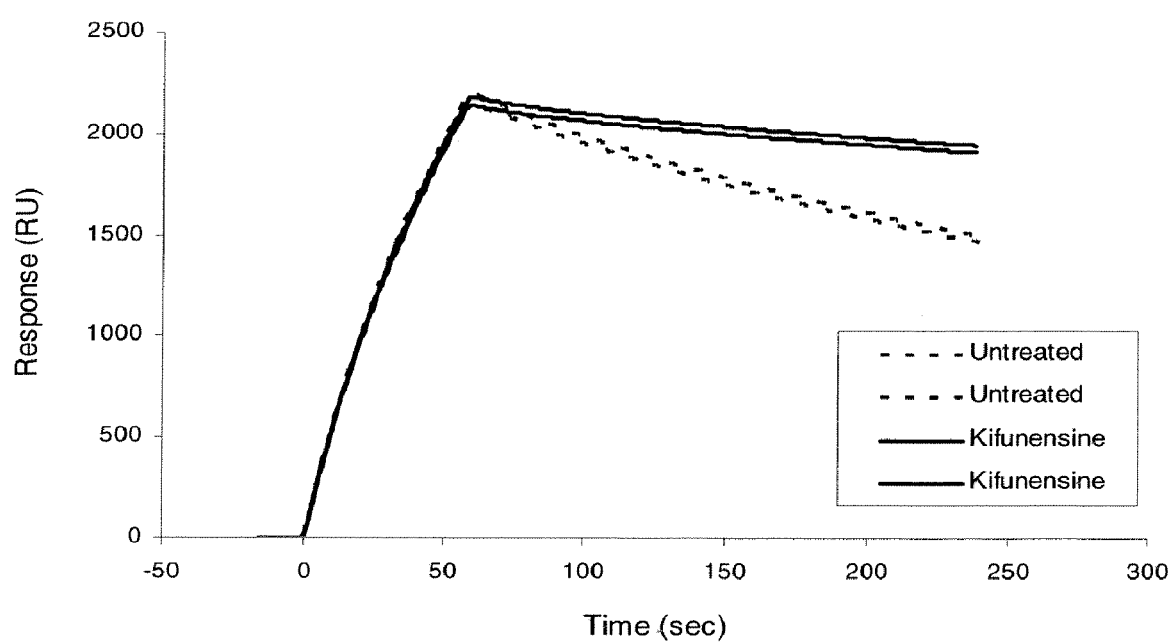
FIG. 14 illustrates results of a surface plasmon resonance analysis of the interaction between FcγRIIIA (Val158) and antibody C from HEK293 cells treated with or without kifunensine. Soluble human FcγRIIIA was captured on the sensor chip, and the binding of antibody C to the immobilized FcγRIIIA was measured.
Figure 15A:
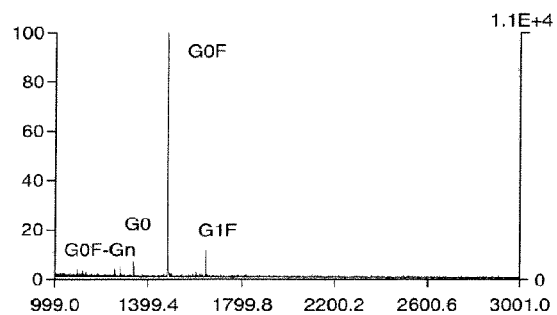
FIG. 15 shows results of a MALDI-TOF mass spectrometry analysis of carbohydrates of TEM mAb A from CHO cells untreated with kifunensine (FIG. 15A) or from CHO cells treated with kifunensine at 4 ng/ml (FIG. 15B), 20 ng/ml (FIG. 15C), 100 ng/ml (FIG. 15D), 500 ng/ml (FIG. 15E), and 2500 ng/ml (FIG. 15F).
Figure 15:
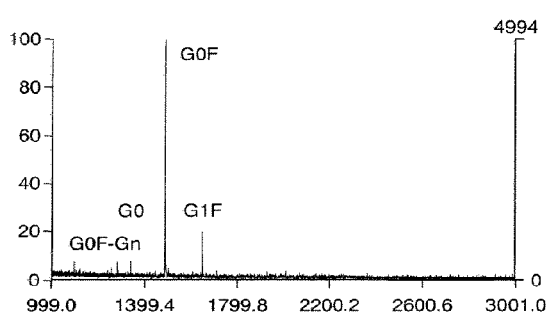
Figure 15C:
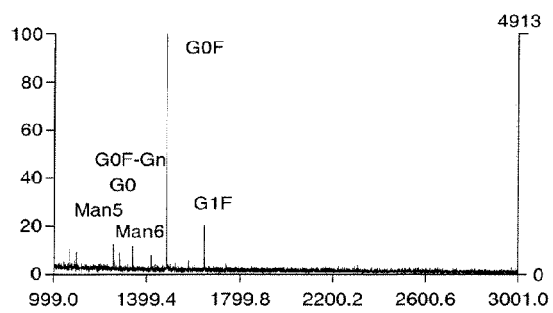
Figure 15D:
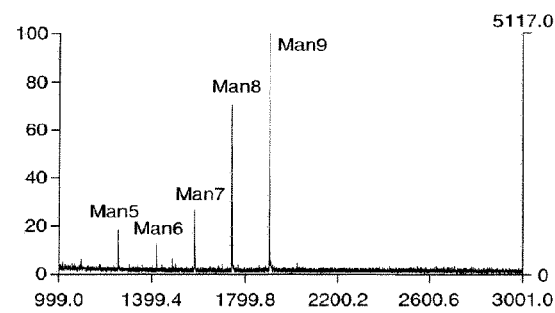
Figure 15E:
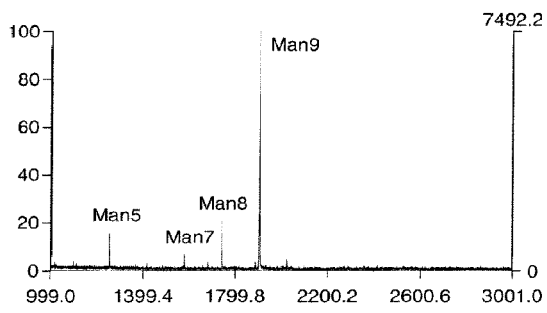
Figure 15F:
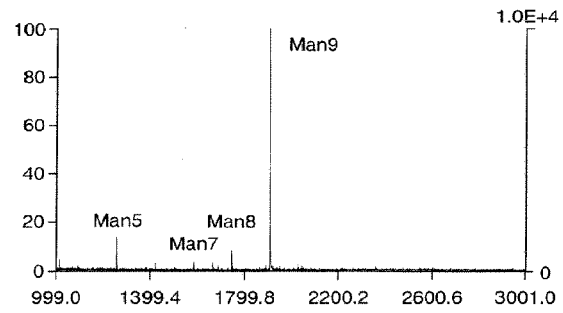
Figure 16A:
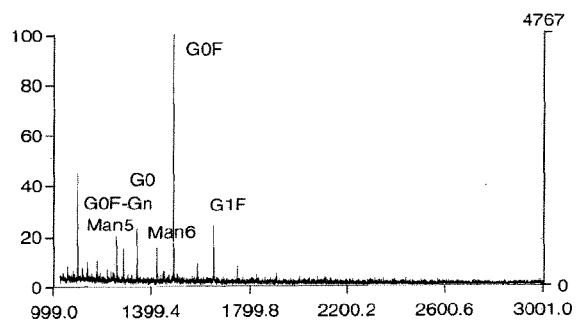
FIG. 16 shows results of a MALDI-TOF mass spectrometry analysis of carbohydrates from TEM mAb A from CHO cells treated with various amounts of kifunensine: 20 ng/ml (FIG. 16A), 40 ng/ml (FIG. 16B), 60 ng/ml (FIG. 16C), 80 ng/ml (FIG. 16D), and 100 ng/ml (FIG. 16E).
Figure 16B:
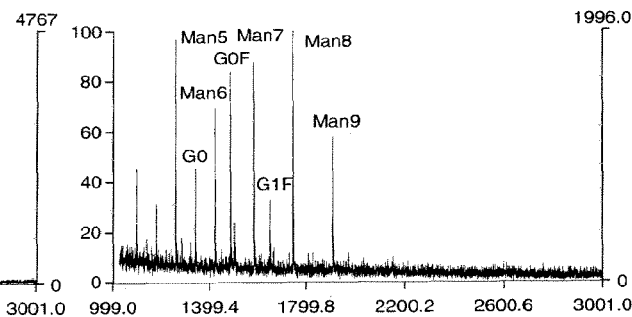
Figure 16C:
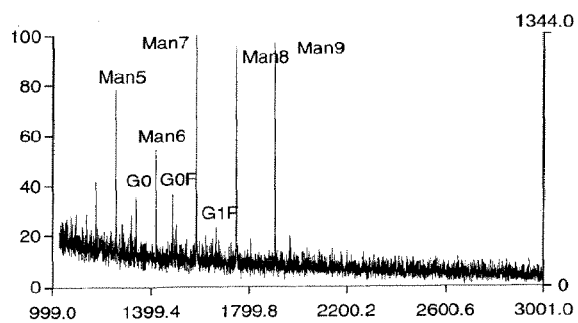
Figure 16D:
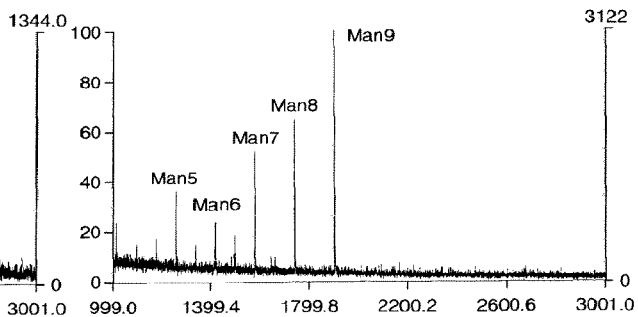
Figure 16E:
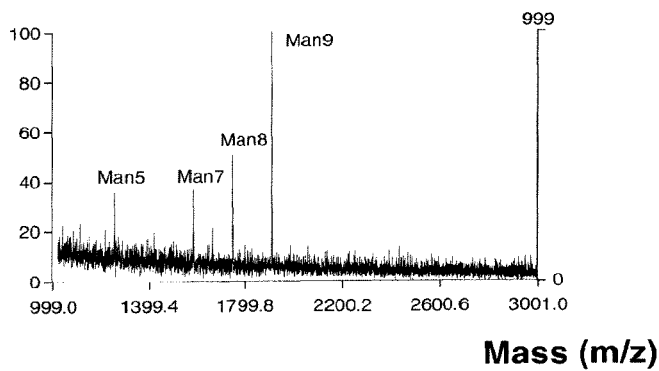

The FcγRIIIA binding of kifunensine-treated antibody C was measured using BIAcore. HPC4-tagged soluble human FcγRIIIA (Val158) was diluted to 30 μg/ml in HBS-P buffer, containing 1 mM $CaCl_2$, and injected into a 14,500 RU Anti-HPC4 chip for 3 min at 5 μl/min. All antibodies were diluted to 100 nM in the same buffer and injected after the capture of soluble FcγRIIIA for 1 min, followed by 3 min dissociation at 30 μl/min. The surface was regenerated with 2 pulses of 5 mM EDTA in HBS-P buffer. The results from the BIAcore® analysis showed higher FcγRIIIA binding of the antibody expressed in the presence of kifunensine as compared to the control antibody (FIG. 14). The results are consistent with the observed ADCC enhancement. The modified antibodies have slower off-rates (see FIG. 14).

Example 12

Titration of Kifunensine Concentration

To investigate the impact of mixed oligomannose and complex-type glycans on antibody function, cells expressing TEM mAb A were treated with various amounts of kifunensine. In the first experiment, a CHO cell clone expressing TEM mAb A was treated with 0, 4, 20, 100, 500 and 2500 ng/ml of kifunensine for 11 days. The medium was harvested, and the antibody was purified using a protein A column. Fractions containing protein peaks were pooled and dialyzed into PBS.

Purity of the six antibody samples was confirmed using a 4-20% gradient SDS-PAGE under reducing conditions, followed by staining with Coomassie blue. The results confirmed that these antibodies were pure.

MALDI-TOF MS analysis was performed on these six samples (shown in FIGS. 15A-15F). The results showed only a small amount of oligomannose structures (Man5/Man6) in the antibody from cells treated with 20 ng/ml kifunensine, while 100 ng/ml kifunensine resulted in complete oligomannose structures.

A second titration experiment was performed with a narrower range of kifunensine concentration, specifically, from 20 to 100 ng/ml. After treatment for 11 days, 50 ml of medium from each treatment condition was harvested, and the antibody was purified. Peak-containing fractions were pooled, buffer-exchanged into PBS using Centricon® filters with repeated centrifugation. Aliquots of TEM mAb A antibody samples were applied to a 4-12% NuPAGE and stained with Coomassie blue to confirm purity.

The results of MALDI-TOF MS performed on these samples are shown in FIGS. 16A-16E. The glycan structures of the antibody from cells treated with 20 and 100 ng/ml kifunensine were similar to those found in the first titration experiment, while kifunensine treatment at 40 and 60 ng/ml concentrations resulted in antibodies with mixed oligomannose and complex-type glycans.

Figure 17A:
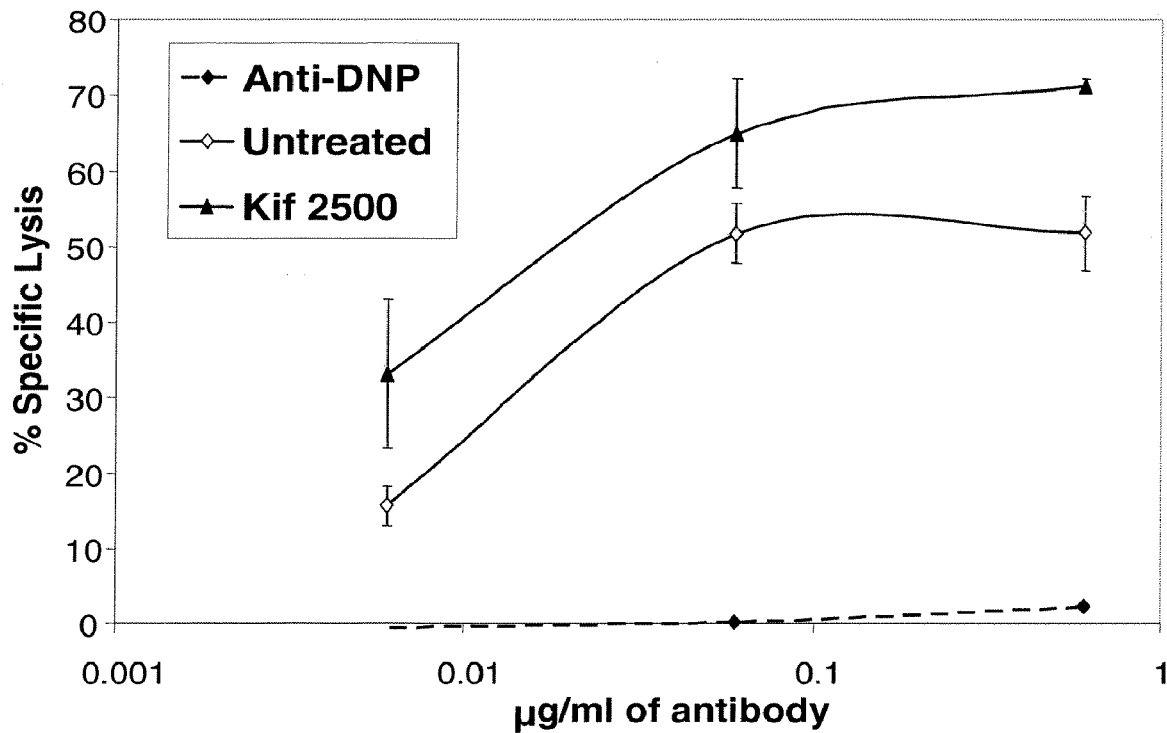
FIG. 17A shows ADCC activity of the antibody expressed in the absence of kifunensisne or in the presence of 2500 ng/ml kifunensine. Anti-DNP antibody was included as a negative control.
Figure 17B:
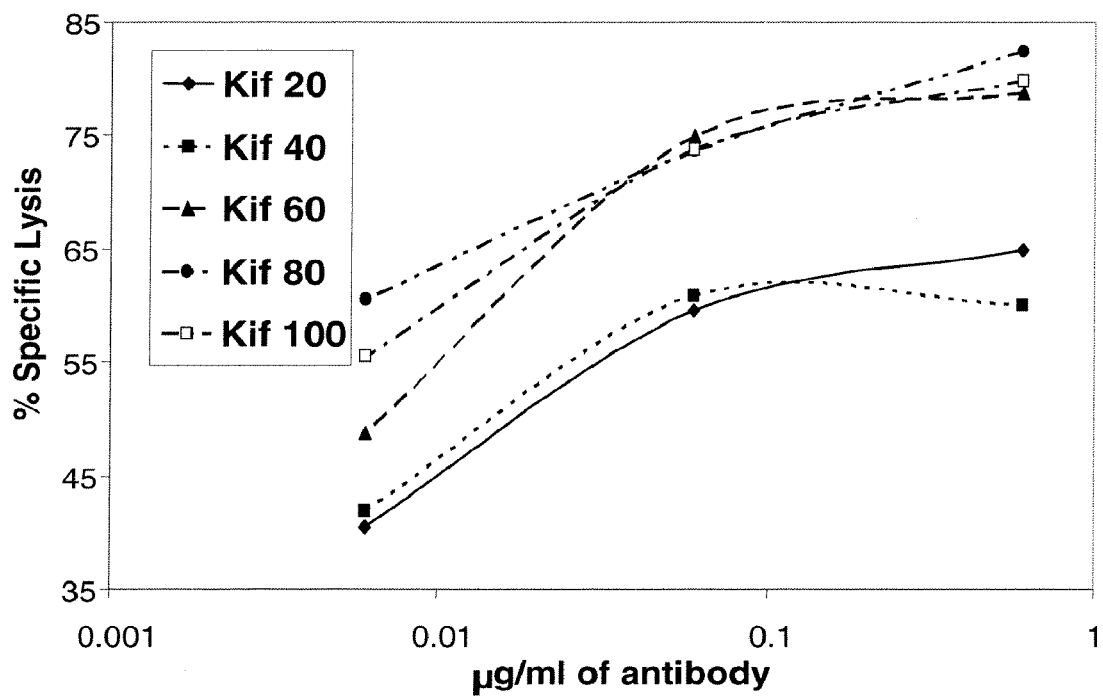
FIG. 17B shows ADCC activity of the same antibody from cells treated with 20, 40, 60, 80 and 100 ng/ml kifunensine.

Further, an ADCC assay was performed. The results showed higher ADCC activity for antibody from cells treated with 2500 ng/ml kifunensine as compared to antibodies produced without any inhibitors in the first titration experiment (FIG. 17A). When five samples from the second titration experiment were compared, the antibodies expressed in the presence of 60, 80 and 100 ng/ml kifunensine showed higher ADCC activity than the antibodies from cells treated with 20 and 40 ng/ml kifunensine. See FIG. 17B.

Figure 18:
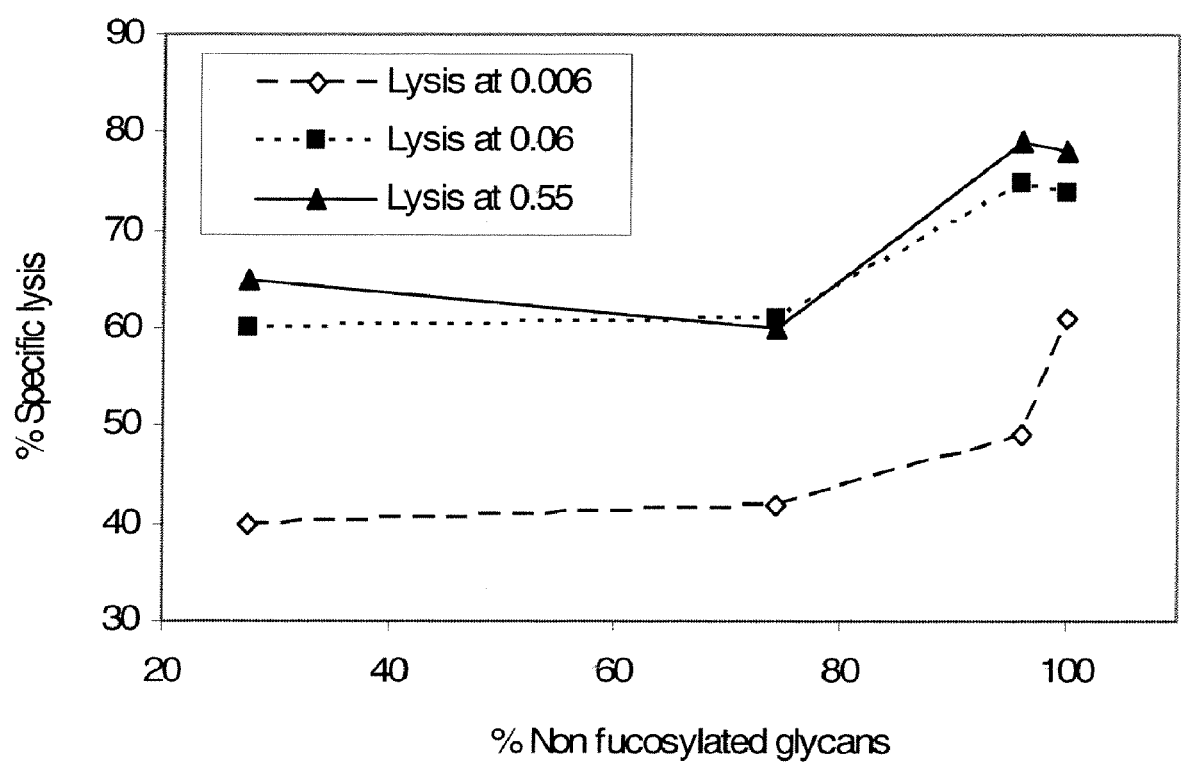
FIG. 18 illustrate the relationship between the percentages of nonfucosylated glycans and specific cytotoxicity at three antibody concentrations (0.006, 0.06 and 0.55 µg/ml). The percentage of nonfucosylated glycans was estimated by calculating the area of each individual glycan peak in MALDI-TOF MS spectra.

The amount of fucosylated and non-fucosylated glycans in antibodies from each kifunensine treatment in the second titration experiment was estimated by calculating the area of each individual glycan peak in MALDI-TOF MS spectra. The percent non-fucosylated glycans was plotted against the percent specific target cell lysis and is shown in FIG. 18. The results suggest that TEM mAb A with more than 80% non-fucosylated glycans has a relatively higher ADCC activity.

In summary, antibodies from cells treated with >80 ng/ml kifunensine showed only oligomannose structures without any fucose. As kifunensine concentration was lowered to 60 ng/ml, and then further to 20 ng/ml, the antibodies exhibited increasing amounts of complex-type glycans with fucose. Higher ADCC activity was achieved with 60 ng/ml or higher kifunensine concentrations which, in turn, produced more than 80% non-fucosylated glycans.

Example 13

Binding of Human Fc Receptors to Antibodies from Cells Treated with Kifunensine

Figure 19A:
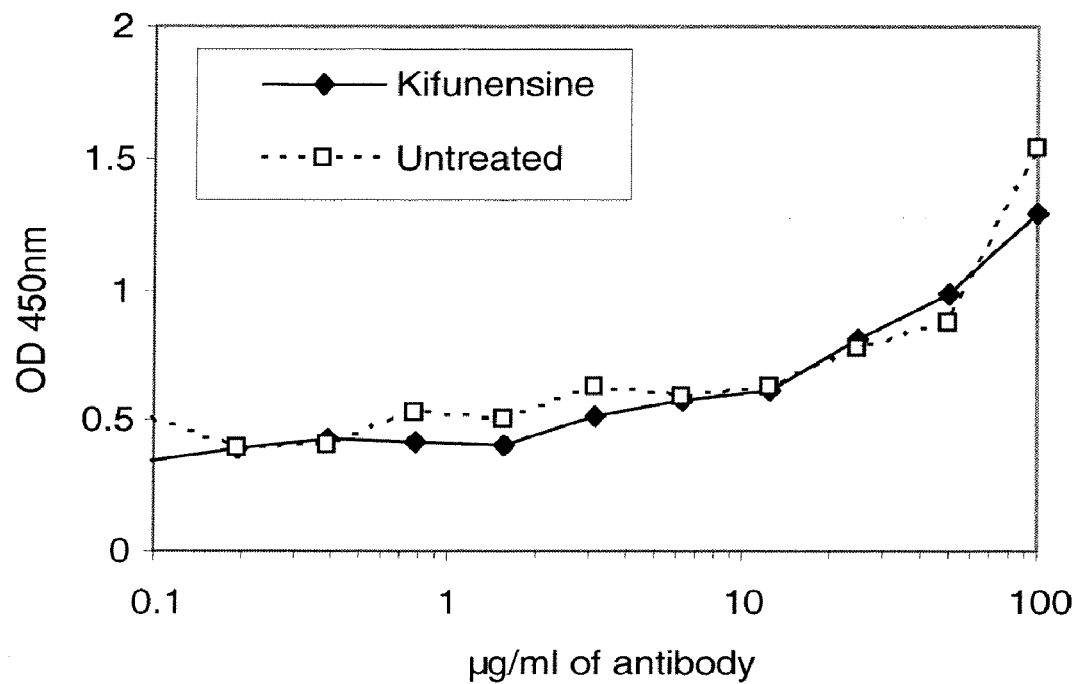
FIG. 19A shows binding of antibody to FcγRIA.
Figure 19B:
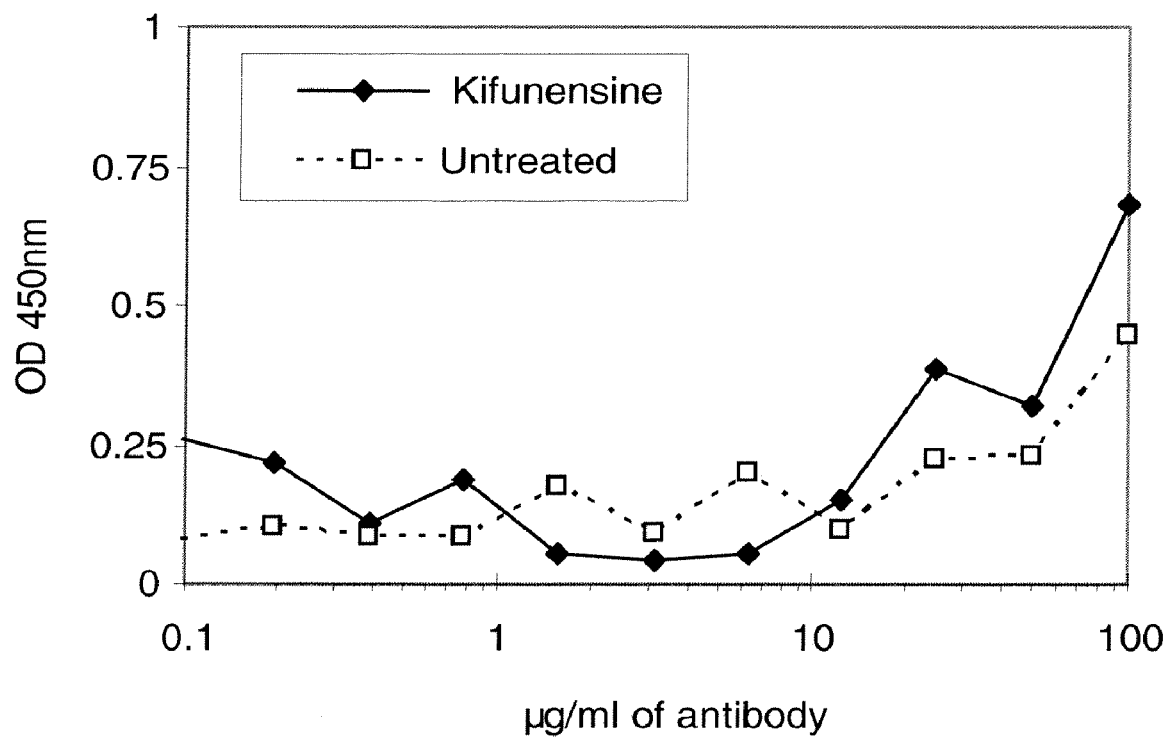
FIG. 19B shows binding of antibody D to FcγRIIA.
Figure 19C:
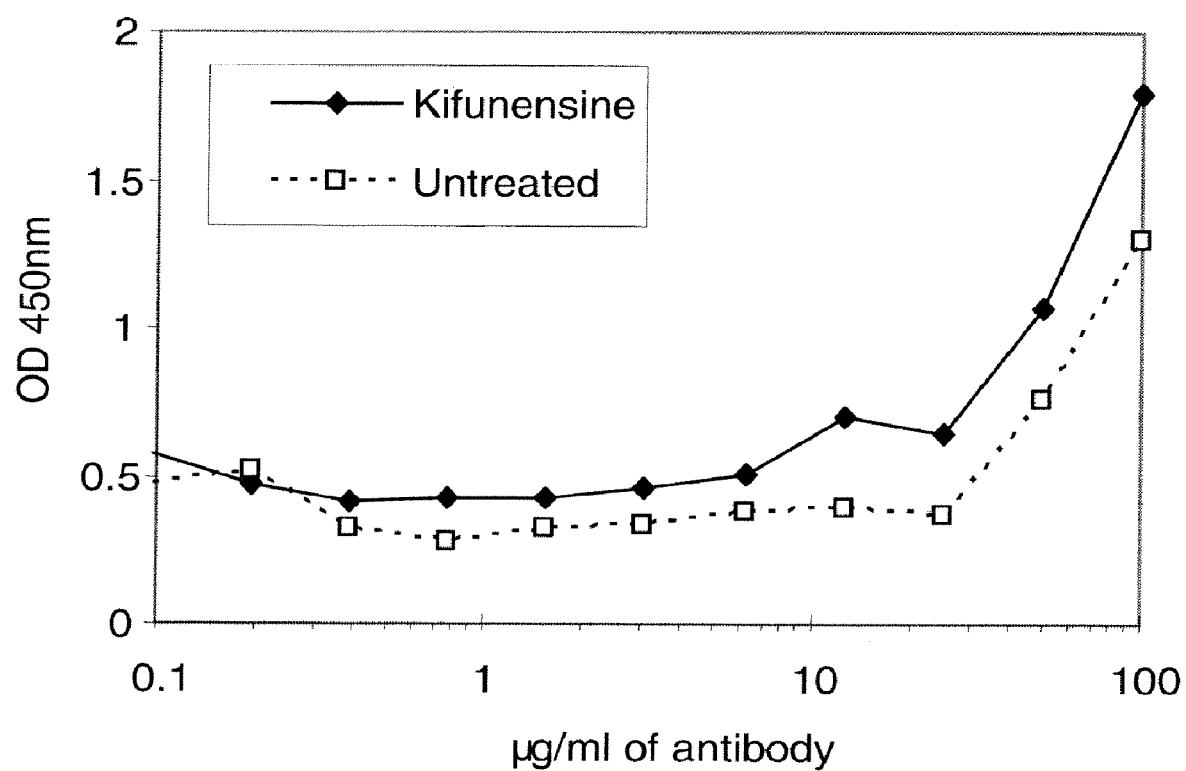
FIG. 19C shows binding of antibody D to FcγRIIB.

Binding of kifunensine-modified antibody D, another anti-tumor antibody, to various recombinant human Fcγ receptors (FcγRI, FcγRIIA and FcγRIIB) was analyzed using an ELISA format binding assay. 96-well microtiter plates were coated with Fcγ receptors from R&D systems at the following concentrations: 0.5 µg/ml of FcγRI, 2.5 µg/ml of FcγRIIA, and 2 µg/ml of FcγRIIB. Wells were washed 3 times with PBS containing 0.1% Tween 20 and then blocked with PBS/1% BSA for 1 hr at room temperature. Antibodies, including antibody D from cells treated with or without kifunensine ranging from 0 to 100 µg/ml, were added to the wells and incubated at room temperature for 2 hrs. Antibody concentrations started at 100 µg/ml and a 1:2 serial dilution was used. Plates were washed 3 times with PBS containing 0.1% Tween 20. Bound antibody was detected using 1-hr incubation with a goat anti-human Fab-HRP (1:1500) in PBS containing 1% BSA at room temperature. Plates were then washed and developed with TMB (BioFX lab) at 15 minutes for FcγRI and FcγRIIB and 30 min for FcγRIIA. Reaction was stopped with 2M $H_2SO_4$ and the absorbance read at 450 nm. Antibody D from cells treated with or without kifunensine bound strongly to the high affinity FcγRI compared to the low affinity receptors, FcγRIIA and FcγRIIB. The results, presented in FIGS. 19A-19C, suggested that kifunensine treatment may improve antibody binding to FcγRIIA and FcγRIIB but not FcγRI.

All numbers expressing quantities of ingredients, cell culture, treatment conditions, and so forth used in the specification, including claims, are to be understood as being modified by the term "about" unless the context requires otherwise. The embodiments within the specification provide an illustration of embodiments of the invention and should not be construed to limit the scope of the invention. All publications, patents, patent applications, and biological sequences cited in this disclosure are incorporated by reference in their entirety.

The invention claimed is:

1. A method of producing a glycosylated monoclonal antibody or Fc fusion protein comprising:
   (a) providing a monoclonal antibody or Fc fusion protein producing cell;
   (b) culturing the cell in the presence of an amount of kifunensine sufficient to produce a monoclonal antibody or Fc fusion protein having at least 50% Man$_{5-9}$(GlcNAc)$_2$ N-glycans, wherein Man8 and Man9-containing N-glycans together are the major species; and
   (c) recovering the glycosylated antibody or Fc fusion protein.

2. The method of claim 1, wherein the amount of kifunensine is less than 1000 ng/ml.

3. The method of claim 1, wherein the amount of kifunensine is less than 500 ng/ml.

4. The method of claim 1, wherein the amount of kifunensine is less than 100 ng/ml.

5. The method of claim 1, wherein the amount of kifunensine is less than 80 ng/ml.

6. The method of claim 1, wherein the amount of kifunensine is at least about 60 ng/ml.

7. The method of claim 1, wherein the amount of kifunensine is about 60 to about 2500 ng/ml.

8. The method of claim 1, wherein the monoclonal antibody or Fc fusion protein has at least 60% Man$_{5-9}$(GlcNAc)$_2$ N-glycans.

9. The method of claim 1, wherein the monoclonal antibody or Fc fusion protein has at least 70% Man$_{5-9}$(GlcNAc)$_2$ N-glycans.

10. The method of claim 1, wherein the monoclonal antibody or Fc fusion protein has at least 90% Man$_{5-9}$(GlcNAc)$_2$ N-glycans.

11. The method of claim 1, wherein the amount of kifunensine is sufficient to produce a monoclonal antibody or Fc fusion protein having less than 30% Man$_5$(GlcNAc)$_2$ and/or Man$_6$(GlcNAc)$_2$ N-glycans.

12. The method of claim 1, wherein the amount of kifunensine sufficient to produce a monoclonal antibody or Fc fusion protein having less than 30% fucosylated N-glycans.

* * * * *

UNITED STATES PATENT AND TRADEMARK OFFICE
CERTIFICATE OF CORRECTION

| | | |
|---|---|---|
| PATENT NO. | : 8,071,336 B2 | Page 1 of 1 |
| APPLICATION NO. | : 12/704990 | |
| DATED | : December 6, 2011 | |
| INVENTOR(S) | : McPherson et al. | |

It is certified that error appears in the above-identified patent and that said Letters Patent is hereby corrected as shown below:

In column 30, lines 37-38, "kifunensine sufficient" should read
--kifunensine is sufficient--.

Signed and Sealed this
Twenty-eighth Day of February, 2012

David J. Kappos
*Director of the United States Patent and Trademark Office*